United States Patent [19]

Yamashita et al.

[11] Patent Number: 5,457,251
[45] Date of Patent: Oct. 10, 1995

[54] METHOD FOR PARTIALLY HYDROGENATING A MONOCYCLIC AROMATIC HYDROCARBON

[75] Inventors: Kunihiko Yamashita, Kurashiki; Hideaki Obana, Kamakura; Issei Katsuta, Kurashiki, all of Japan

[73] Assignee: Asahi Kasei Kogyo Kabushiki Kaisha, Japan

[21] Appl. No.: 6,873

[22] Filed: Jan. 21, 1993

[30] Foreign Application Priority Data

Jan. 24, 1992 [JP] Japan .................. 4-032936

[51] Int. Cl.⁶ .................................. C07C 5/11
[52] U.S. Cl. .................. 585/269; 585/266; 585/273; 585/277; 422/215
[58] Field of Search .................. 585/266, 269, 585/273, 277, 922, 271; 422/215, 228, 230

[56] References Cited

U.S. PATENT DOCUMENTS

| 3,130,014 | 4/1964  | Stanton ............................. 23/288 |
| 3,703,558 | 11/1972 | Levine ............................ 260/666 P |
| 3,767,720 | 10/1973 | Drinkard ............................. 585/267 |
| 3,912,787 | 10/1975 | Nowack et al. ................... 260/667 |
| 4,055,512 | 10/1977 | Kageyama et al. ............... 252/441 |
| 4,495,373 | 10/1985 | Niwa et al. ....................... 585/269 |
| 4,734,536 | 3/1988  | Nagahara et al. ................ 585/269 |
| 5,157,179 | 10/1992 | Setoyama et al. ................ 585/266 |

FOREIGN PATENT DOCUMENTS

| 0466128   | 1/1992 | European Pat. Off. . |
| 0562113A1 | 9/1993 | European Pat. Off. . |
| 2-16736   | 4/1990 | Japan . |
| 2-19098   | 4/1990 | Japan . |
| 2-19096   | 4/1990 | Japan . |
| 3-5370    | 1/1991 | Japan . |
| 3-5371    | 1/1991 | Japan . |

OTHER PUBLICATIONS

European Search Report of May 6, 1993.

*Primary Examiner*—P. Achutamurthy
*Attorney, Agent, or Firm*—Pennie & Edmonds

[57] ABSTRACT

Disclosed is a method for partially hydrogenating a monocyclic aromatic hydrocarbon to produce a cycloolefin, comprising reacting a monocyclic aromatic hydrocarbon with hydrogen in the presence of a particulate hydrogenation catalyst comprised mainly of metallic ruthenium, in a reaction system comprising a continuous aqueous phase having the particulate hydrogenation catalyst suspended therein, an oil phase containing the monocyclic aromatic hydrocarbon, and a gaseous phase comprising hydrogen gas, while applying a shearing force to the reaction system at a specific maximum shear rate. By the method of the present invention, not only can a cycloolefin be produced at high selectivity and in high yield, but also the catalytic activity can be stably maintained at a high level for a prolonged period of time.

17 Claims, 6 Drawing Sheets

METHOD FOR PARTIALLY HYDROGENATING A MONOCYCLIC AROMATIC HYDROCARBON

BACKGROUND OF THE INVENTION

1. Field of The Invention

The present invention relates to a method for partially hydrogenating a monocyclic aromatic hydrocarbon to obtain a cycloolefin. More particularly, the present invention is concerned with a method for partially hydrogenating a monocyclic aromatic hydrocarbon to obtain a cycloolefin, in which the hydrogenation reaction is conducted in a reaction system comprising a continuous aqueous phase having a particulate hydrogenation catalyst suspended therein and comprised mainly of metallic ruthenium, an oil phase containing a monocyclic aromatic hydrocarbon and a gaseous phase comprising hydrogen gas, while applying a shearing force to the reaction system at a specific maximum shear rate. By the method of the present invention, not only can a cycloolefin be produced at high selectivity and in high yield, but also the catalytic activity can be stably maintained at a high level for a prolonged period of time.

2. Discussion of Related Art

Cycloolefins are of high commercial value as intermediates for the manufacture of organic chemical products and are particularly important as materials for the production of polyamides and lysines.

As a method for partially hydrogenating a monocyclic aromatic hydrocarbon to produce a cycloolefin, there has conventionally been proposed a method in which use is made of water and a particulate hydrogenation catalyst comprised mainly of metallic ruthenium (see Japanese Patent Application Laid-Open Specification Nos. 61-50930, 62-45544, 62-81332, 62-205037 and 63-17834; these Japanese patent documents correspond to U.S. Pat. No. 4,734,536).

For example, Japanese Patent Application Laid-Open Specification No. 63-17834 mentioned above discloses a working Example in which partial hydrogenation of a monocyclic aromatic hydrocarbon is conducted using a particulate hydrogenation catalyst comprised mainly of metallic ruthenium having an average crystallite diameter of 200 Å or less, a zinc compound as a promoter, and zirconium oxide or hafnium oxide as an additive. In this working Example, an autoclave having an agitator provided therein is charged with water, the above-mentioned catalyst, promoter and additive, and an oil containing benzene and then, the resultant mixture is acidified with a customary acid and the reaction is conducted at a temperature of between 25° and 250° C. under a hydrogen partial pressure of between 5 and 150 kg/cm$^2$ for a period of time of from several minutes to 2 hours under high-speed agitation while supplying hydrogen gas, to thereby produce cyclohexene. Then, the produced cyclohexene is isolated from the oil phase.

The reaction system used in the above-mentioned conventional method is a heterogeneous system comprised of an oil phase containing a monocyclic aromatic hydrocarbon, an aqueous phase comprising water, a solid phase comprising a particulate hydrogenation catalyst suspended in the aqueous phase, and a gaseous phase comprising hydrogen gas being blown into the reaction system. In the conventional method using such a reaction system, difficult problems have frequently been encountered. Illustratively stated, the conventional method has problems in that when the oil-water mixing and/or gas-liquid mixing is insufficient, the activity of the hydrogenation catalyst in the reaction system cannot be fully exerted and therefore the reaction yield becomes considerably low. On the other hand, when the gas-liquid mixing is too vigorous, not only is the activity of the hydrogenation catalyst rapidly lowered during the reaction, but also the separation between the oil phase and the aqueous phase for obtaining the produced cyclohexene contained in the oil phase needs a long period of time, thus requiring a large stationary zone.

Thus, the conventional method for partially hydrogenating a monocyclic aromatic hydrocarbon has been unsatisfactory not only in that the desired cycloolefin cannot be stably obtained in high yield, but also in that the separation of the oil phase from the aqueous phase after the reaction cannot be efficiently conducted. Therefore, the conventional method cannot be satisfactorily put to practical use.

SUMMARY OF THE INVENTION

With a view toward developing a method for partially hydrogenating a monocyclic aromatic hydrocarbon which is free from the above-mentioned drawbacks inevitably accompanying the conventional method, the present inventors have conducted extensive and intensive studies. As a result, it has unexpectedly been found that this goal can be attained by strictly controlling the conditions under which the continuous aqueous phase, the oil phase and the gaseous phase of the reaction system are brought into contact with one another. More particularly, the present inventors have found that the problems of the prior art can be successfully solved by a method in which the hydrogenation reaction is conducted while applying a shearing force to the reaction system at a specific maximum shear rate, so that the oil phase and the gaseous phase are dispersed in the continuous aqueous phase as globules and as bubbles, respectively. Based on this novel finding, the present invention has been completed.

It is, therefore, an object of the present invention to provide a method for partially hydrogenating a monocyclic aromatic hydrocarbon, which can advantageously be used for producing a cycloolefin on a commercial scale, and in which not only can a deterioration of the hydrogenation catalyst during the reaction be minimized, but also high yield of and high selectivity for a cycloolefin can be attained and maintained for a prolonged period of time, and the oil-water separation after the reaction can also be readily carried out.

The foregoing and other objects, features and advantages of the present invention will become apparent from the following detailed description and appended claims taken in connection with the accompanying drawings.

BRIEF DESCRIPTION OF THE DRAWINGS

In the drawings:

In FIGS. 1 through 5, like parts or portions are designated by like numerals. Vacant circles in FIGS. 1 to 3 indicate gas bubbles and oil globules, and dots indicate a hydrogenation catalyst.

DETAILED DESCRIPTION OF THE INVENTION

Figure 1:
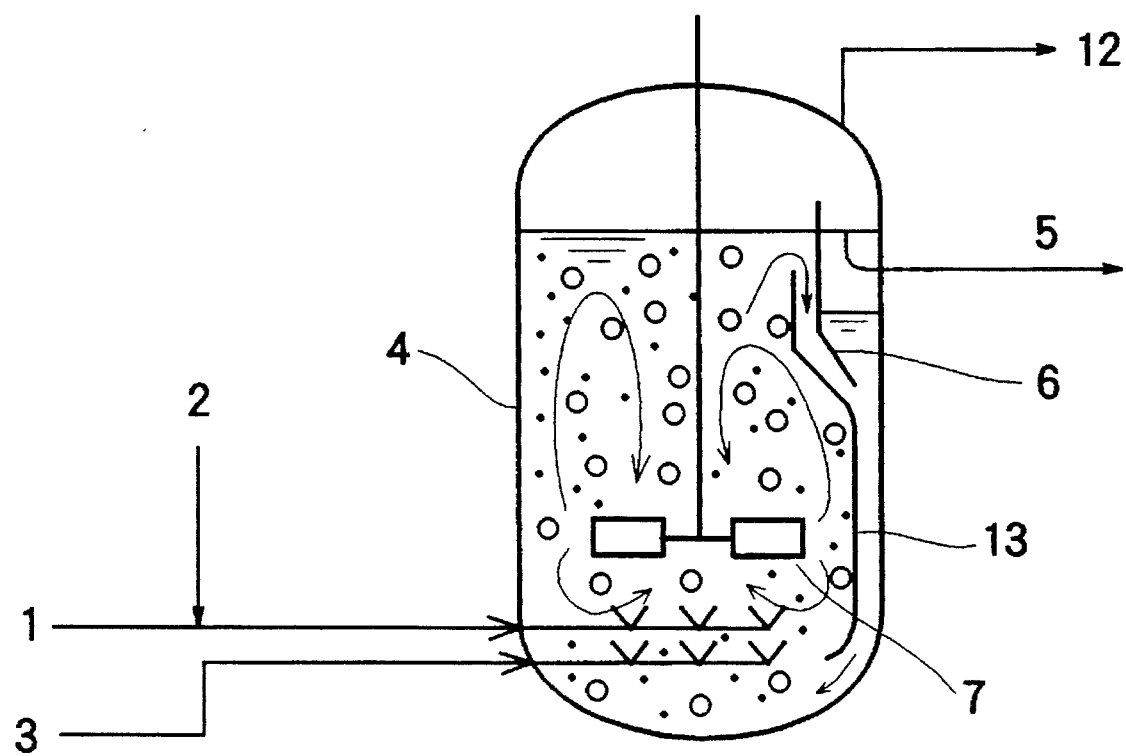
FIG. 1 is a diagrammatic view illustrating one mode of the method of the present invention, in which a reactor is shown in cross-section to show the interior thereof.

Essentially, according to the present invention, there is provided a method for partially hydrogenating a monocyclic aromatic hydrocarbon to produce a cycloolefin, comprising reacting a monocyclic aromatic hydrocarbon with hydrogen in the presence of a particulate hydrogenation catalyst comprised mainly of metallic ruthenium, in a reaction system comprising:

a continuous aqueous phase having the particulate hydrogenation catalyst suspended therein;

an oil phase containing the monocyclic aromatic hydrocarbon; and a gaseous phase comprising hydrogen gas, while applying a shearing force to the reaction system at a maximum shear rate of between about 50 and about 2000/sec, so that the oil phase and the gaseous phase are dispersed in the continuous aqueous phase as globules and as bubbles, respectively.

In the method of the present invention, the reaction of a monocyclic aromatic hydrocarbon (as an oil phase) with hydrogen (as a gaseous phase) is conducted in a continuous aqueous phase comprising water and a particulate hydrogenation catalyst suspended therein. The catalyst is comprised mainly of metallic ruthenium crystallites, and may further contain a zinc compound and optionally other metal compounds.

In the method of the present invention, the gaseous phase comprises hydrogen gas as a main component, and may also contain vapors of a monocyclic aromatic hydrocarbon, a cycloolefin, naphthene, water and the like, and impurities which are contained in the hydrogen gas, such as methane and ethane. The oil phase contains a monocyclic aromatic hydrocarbon as a main component, and may also contain a cycloolefin, a naphthene, water and hydrogen. The above-mentioned aqueous phase comprises water as a main component, and may also contain a zinc compound derived from the catalyst, and a monocyclic aromatic hydrocarbon, a cycloolefin, naphthene and hydrogen. As mentioned above, the particulate hydrogenation catalyst is comprised mainly of metallic ruthenium crystallites, and optionally contains a dispersant (such as hafnium oxide and zirconium oxide) and the like, which constitute a solid phase which is suspended in the continuous aqueous phase.

The reaction mechanism involved in the method of the present invention is explained below, taking as an example the case in which benzene is used as the monocyclic aromatic hydrocarbon. In the reaction system, hydrogen of the gaseous phase is caused to be diffused and dissolved in the continuous aqueous phase having the hydrogenation catalyst suspended therein, through a gas-liquid interface which is present in contact with the aqueous phase. Hydrogen is also dissolved into the oil phase, and some hydrogen is then diffused and dissolved into the continuous aqueous phase through the oil phase. The hydrogen gas having been diffused and dissolved in the continuous aqueous phase is adsorbed onto a number of active sites on the surface of the particulate hydrogenation catalyst. On the other hand, benzene contained in the oil phase is diffused and dissolved into the continuous aqueous phase through an oil-water interface which is present in contact with the aqueous phase and then, adsorbed onto the above-mentioned active sites on the surface of the catalyst, so that the benzene is caused to be reacted with the hydrogen at the active sites, to thereby produce cyclohexene. Then, the produced cyclohexene is released from the catalyst and then, diffused and dissolved into the continuous aqueous phase. The cyclohexene is then transferred from the continuous aqueous phase to the oil phase through the oil-water interface. The cyclohexene can be isolated from the oil phase. As is apparent from the above, in the reaction system of the method of the present invention, mass transfers occur.

The hydrogenation of benzene to cyclohexane involves two reaction routes. One is an indirect, successive reaction route in which benzene is first partially hydrogenated to produce cyclohexene and then the cyclohexene is further hydrogenated to produce a stable compound, cyclohexane. The other is a direct reaction route in which benzene is directly converted to cyclohexane. Of these two reaction routes, the indirect, successive reaction route is predominant.

Cyclohexene which is a desired product of the present invention, is an intermediate product in the indirect, successive reaction route. Accordingly, in the present invention the rate of the reaction in which benzene is partially hydrogenated to cyclohexene should be increased, while the reaction from cyclohexene to cyclohexane should be inhibited. For achieving this, it is requisite that the benzene concentration of an aqueous phase be increased, while produced cyclohexene be quickly released from the hydrogenation catalyst to thereby avoid re-adsorption of the produced cyclohexene onto the hydrogenation catalyst. For meeting this requirement, the presence of an oil phase to extract the produced cyclohexene from the aqueous phase is indispensable. For example, when only a small amount of benzene is incorporated in a reaction system consisting of water and a catalyst which is devoid of an oil phase and a hydrogenation reaction is carried out, the yield of cyclohexene is very small. This indicates that in a heterogeneous reaction as mentioned above, mass transfers are important, which involve e.g., the diffusion of reactants or products to phase interfaces and the diffusion of reactants or products through phase interfaces.

In a heterogeneous reaction system as mentioned above, for ensuring quick mass transfers so that the reaction occurring on a hydrogenation catalyst for producing cyclohexene by the hydrogenation of benzene becomes rate-limiting, it is important to effect appropriate mixing and dispersion of a gaseous phase, an aqueous phase, an oil phase and a solid phase so as to increase interfacial areas between the four phases.

The mixing and dispersion have three roles. One is to finely disperse gas bubbles in the aqueous phase to thereby cause hydrogen gas to be effectively absorbed in the aqueous phase. Another is to finely disperse oil globules to thereby increase the mass transfer rates of benzene and produced cyclohexene at the interface between the oil phase and the aqueous phase in which the catalyst is present. The remainder is to suspend and disperse the catalyst in the aqueous phase. Among these, the most important role is to finely disperse gas bubbles in the aqueous phase, as described later.

With respect to the rate of the reaction in which benzene is hydrogenated to cyclohexene and to the selectivity for cyclohexene, the inventors have analyzed experimental data obtained using an autoclave type reactor provided with an agitator. As a result, it has been found that as a shearing force is increased while maintaining a hydrogen pressure at a high level, the rate of the conversion of benzene is increased until reaching a substantially constant value, after which the conversion rate is slowly, slightly decreased. The phenomenon that the rate of the conversion of benzene becomes substantially constant indicates that the hydrogenation on the catalyst, rather than mass transfers, is a rate-limiting step. On the other hand, the selectivity for cyclohexene is increased with the increase of the shearing force, and there is a tendency that the selectivity for cyclohexene is increased even after the rate of the hydrogenation on the catalyst has reached a substantially constant value. For these phenomena, the following reaction mechanism can be postulated.

That is, as a shearing force is increased while maintaining a hydrogen pressure at a high level, the concentration of hydrogen dissolved in the aqueous phase becomes higher. Then in accordance with the increase of the hydrogen concentration of the aqueous phase, the concentration of hydrogen adsorbed onto the active sites of the hydrogenation catalyst is increased, and the amount of cyclohexene adsorbed in an equilibrium relationship onto the active sites is decreased, so that the amount of cyclohexene which quickly migrates into oil globules from the aqueous phase is increased.

Illustratively stated, the inventors have found that for increasing the selectivity for cyclohexene, it is requisite that shearing force be applied so as to cause hydrogen gas to be present in the reaction system in the form of fine bubbles, thereby ensuring large interfacial areas between the gaseous phase and the liquid phases and accordingly keeping the concentration of dissolved hydrogen in the aqueous phase at a high level.

It is preferred that a large number of minute hydrogen gas bubbles be present in the reaction system. With the progress of the hydrogenation reaction, the hydrogen gas present in the gas bubbles is dissolved into the aqueous phase. By the dissolution of hydrogen gas, the size of the gas bubbles is decreased to cause the gas bubbles to finally disappear or to be released from a gas-liquid free surface at the top of the reaction system. The smaller the diameter of gas bubbles, the greater the absorption of hydrogen gas into the aqueous phase. However, rendering the bubble diameter too fine, does not bring about more appreciable effect on the absorption of hydrogen gas into the aqueous phase. On the other hand, a large amount of energy is required for rendering the gas bubbles fine. Therefore, the diameter of gas bubbles has a lower limit. The volume average diameter (hereinafter referred to simply as "average diameter") of gas bubbles in the reaction system, is preferably in the range of between about 0.4 and about 20 mm, more preferably between about 0.5 and about 10 mm.

The average diameter of gas bubbles can be measured by a photographic method in which the gas bubbles in the reactor are photographed through a peep window provided in the side wall of the reactor and the diameters of the bubbles are measured, thereby determining an average value.

The rate at which hydrogen gas is blown into the reaction system is such that hydrogen gas is supplied in a reaction equimolar amount or more which is required for maintaining a predetermined reaction pressure. Unreacted hydrogen gas is released from the reaction system through a gas-liquid free surface thereof, and it is desired to allow the unreacted hydrogen released from the reaction system to be absorbed back into the reaction system through the free surface in as much an amount as possible. The larger the quantity of the hydrogen gas bubbles in the reaction system, the larger the gas-liquid interfacial area. Therefore, from the viewpoint of facilitating the reaction, it is preferred to increase the quantity of the hydrogen gas bubbles. However, when the quantity of hydrogen gas bubbles is increased to a certain level, the effect of facilitating the reaction cannot be improved any more even when the quantity of the gas bubbles is further increased. In general, the volume ratio (i.e., so-called "gas hold-up") of hydrogen gas bubbles to the liquid in the reaction system is preferably between about 0.002 and about 0.2, more preferably between about 0.004 and about 0.15.

It is desired that the dispersion of the gas bubbles in the reaction system be uniform. However, the state of the dispersion of the gas bubbles is not particularly limited as long as the gas bubbles are dispersed to such an extent that the concentration of dissolved hydrogen in the aqueous phase is not extremely non-uniform. In the method of the present invention, the reaction system is agitated and, therefore, it is less likely that the concentration of dissolved hydrogen in the aqueous phase becomes extremely non-uniform.

The present inventors have made studies as to which of the oil phase and the aqueous phase should be employed as a continuous phase. As a result, they have found that when the catalyst concentration of an aqueous solution is constant, the rate of reaction per unit weight of the catalyst solution is constant, and that, therefore, when the aqueous phase is a continuous phase and the oil phase is a dispersed phase, the volume of the reactor can be smaller than in the opposite case. Therefore, in the present invention, the aqueous phase and the oil phase are, respectively, employed as a continuous phase and a dispersed phase. The volume ratio of the oil phase to the aqueous phase in the reaction system is preferably between about 0.01 and about 1.5, more preferably between about 0.02 and about 1.0.

As in the case of the gas-liquid interface, the oil-water interfacial area is desirably as large as possible. The globule size of the oil phase is desirably as small as possible so as to render the oil-water interfacial area satisfactorily large, thereby increasing the monocyclic aromatic hydrocarbon concentration of the aqueous phase. When a large number of fine oil globules are present in the reaction system, an oil-water interfacial area satisfactory for mass transfer can be provided. However, when the globule size of the oil phase is too small, it takes too much time for oil globules to unite with each other, so that the time necessary for separating the oil phase from the aqueous phase after the reaction is prolonged. In this case, when it is desired to shorten the separating time, it is necessary to increase the space of a stationary zone or the size of an oil phase-aqueous phase separator to be provided for effecting the separation. Thus, it is desired that the contact between the oil phase and the aqueous phase be conducted under such conditions that the size of the oil globules are not too small. From the viewpoint of assuring a satisfactory oil-water interfacial area and preventing the prolongation of the time necessary for oil-water separation, it is preferred that the volume average diameter (hereinafter referred to simply as "average diameter") of the oil globules be between about 0.02 and about 30 mm. The average oil globule diameter is more preferably between about 0.05 and about 10 mm.

In the present invention, the time necessary for separating the reaction system in the reactor into the oil phase and the aqueous phase is determined by the following method. A predetermined feed stock solution is charged into a 4-liter stainless steel-made autoclave having a peep window in the wall thereof and the operation is started by supplying the feed stocks while agitating. When the supply of the feed stocks and the agitation are stopped, the movement of the reaction system caused by the external force stops, and the oil globules dispersed in the aqueous phase begin to spontaneously ascend and these globules unite with each other in the upper portion of the reaction system in the reactor, thereby gradually forming a continuous oil phase above the continuous aqueous phase. The level of the lower surface of the continuous oil phase (i.e., the level of the interface between the continuous oil and aqueous phases) continues to be lowered until the oil globules present between the continuous oil phase and the continuous aqueous phase have completely united together with the continuous oil phase. When the oil globules have disappeared, the level of the lower surface of the continuous oil phase (i.e., the level of the interface between the continuous oil and aqueous phases) becomes stable. The time between the moment at which the movement of the reaction system caused by the external force stops and the moment at which the level of the lower surface of the continuous oil phase becomes stable is defined as the time necessary for separating the oil phase from the aqueous phase (i.e., the oil-water separating time). In the method of the present invention, when the volume of the reaction system is, for example, 4 liters, the oil-water separating time is generally between about 8 and about 60 seconds. When the volume of the reaction system is large, it takes a longer time for the oil globules to ascend to form a continuous oil phase, so that the oil-water separating time is prolonged.

As a method for measuring the diameter of oil globules dispersed in an aqueous phase, a light transmission method, a photographic method and the like are known. In the method of the present invention, the reaction system is opaque, so that the light transmission method is not suitable for use in the present invention. Therefore, in the present invention, the photographic method is preferably employed for measuring the diameter of the oil globules dispersed in the aqueous phase. For example, 350 ml of water containing 0.2% by weight of surfactant is placed in a transparent pressure vessel having a volume of 1000 ml, the internal pressure of which is kept at a level slightly lower than the internal pressure of the reactor, and about 10 ml of the reaction mixture containing oil globules is sampled from the reactor (in which the reaction system is in a circulated state) through a sampling nozzle and the sampled reaction mixture is placed in the transparent pressure vessel. The sampled reaction mixture is caused to be diluted with the water in the pressure vessel and the oil globules ascend to the surface of the water. After the oil globules reach the surface of the water, a photograph of the oil globules is taken. The photograph is magnified, for example, 2 to 100 times, and the diameters of about 150 to about 350 oil globules are measured by means of an ordinary measure, thereby determining an average value, which is taken as a volume average oil globule diameter. When the size of the oil globules is large and thus the globules are likely to unite with each other during the sampling before taking a photograph, the size of the equipment for the sampling is increased, thereby preventing the uniting of the oil globules during the sampling.

Alternatively, measurement of the diameter of the oil globules can be conducted, without sampling of the reaction mixture, by photographing the oil globules in the reactor through a peep window directly provided in the wall of the reactor, as in the case of determining the average diameter of gas bubbles.

As in the case of the dispersion of the hydrogen gas bubbles, it is not necessary that the dispersion of the oil globules be uniform. The dispersion state of the oil globules is not particularly limited as long as the oil globules are dispersed to such an extent that the concentration of the monocyclic aromatic hydrocarbon dissolved in the aqueous phase is not extremely non-uniform. In the method of the present invention, the reaction system is agitated and, therefore, it is less likely that the concentration of dissolved monocyclic aromatic hydrocarbon in the aqueous phase becomes extremely non-uniform.

In the method of the present invention, the oil globules constituting the oil phase and the hydrogen gas bubbles constituting the gaseous phase are present in the continuous aqueous phase having the particulate catalyst suspended therein. As mentioned above, there is no particular limitation with respect to the dispersion state of the oil globules and the gas bubbles, and the dispersion thereof may or may not be uniform.

With respect to the method for dispersing the oil phase and the gaseous phase in the continuous aqueous phase to form oil globules and gas bubbles, the oil phase and the gaseous phase can be mechanically dispersed in the aqueous phase by applying a shearing force to the reaction system. The application of the shearing force can be performed, for example, by a method using an agitator or a method in which the reaction system is flowed through a reactor tube at high flow rate, as described later in detail.

For producing fine oil globules and fine gas bubbles, it is required to apply an external force (shearing force) to the oil phase and the gaseous phase for a period of time sufficient to cause these phases to be divided, the external force being sufficient to overwhelm the interfacial pressure and viscous stress of the fluids. A satisfactory external force can be provided by increasing the shear rate. The terminology "shear rate" means a velocity gradient of a fluid. For example, when an agitator is used to provide the shearing force, the shear rate is defined as a gradient of the velocity distribution of a liquid flow produced by the agitating blades. Shear rate can be measured by means of a heat wave velocimeter, a laser velocimeter or the like. The method for measuring shear rate is described in "Fluid Mixing Technology", written by James Y. Oldshue, Ph.D., published by McGraw-Hill, Inc.

As mentioned above, when the shearing force applied to the reaction system is too large, the rate of the lowering of the catalytic activity is markedly increased. The exact reason for this has not yet been elucidated, but an assumption can be made as follows. The activity of a particulate hydrogenation catalyst comprising crystallites of metallic ruthenium and/or agglomerated crystallites of metallic ruthenium is determined by the surface area of the crystallite, and when the quantity of the catalyst is not changed, the catalytic activity is directly proportional to the reciprocal of the diameter of the crystallite. That is, when the crystallite diameter is reduced, not only is the catalytic activity increased, but also it is believed that, as described in Japanese Patent Application Laid-Open Specification No. 61-50930, the area of the sites on the surface of the crystallites, which are suitable for the formation of cyclohexene, is increased, thereby improving the selectivity for cyclohexene. For use as a catalyst, the metallic ruthenium crystallites are suspended in the aqueous phase. In this case, it is believed that when too large a shearing force is applied to the reaction system, agglomeration of crystallites is disadvantageously promoted, leading to an increase in the crystallite diameter of the catalyst. For example, when the shearing force is too large, the crystallite diameter of the metallic ruthenium is increased with time during the reaction, thereby lowering not only the catalytic activity but also the selectivity for cyclohexene. This phenomenon is likely to occur even in the presence of a dispersant for dispersing metallic ruthenium crystallites. For attaining a catalytic activity which is stable for a long period of time, it is desired to apply a shearing force of an appropriate strength which does not cause the above-mentioned phenomenon. The strength of the shearing force can be expressed by maximum shear rate. In the method of the present invention, the maximum shear rate is between about 50 and about 2000/sec, preferably between about 70 and about 1500/sec (herein, "/sec" means the reciprocal of a second). The terminology "maximum shear rate" is defined as the maximum gradient of the velocity distribution of a liquid flow produced, for example, by agitating blades. The direction of the liquid flow is not particularly limited and may be vertical or horizontal. Accordingly, with respect to the maximum shear rate, there is no restriction on the direction of the shearing force. The higher the maximum shear rate, the smaller the oil globules and gas bubbles become.

The particulate metallic ruthenium as a hydrogenation catalyst is suspended in the aqueous phase, in the presence or absence of a dispersant, such as hafnium oxide and zirconium oxide. The dispersion of the particulate metallic ruthenium is desired to be as uniform as possible. Especially when the agitating force applied to the reaction system is relatively small and the dispersion of the catalyst is so non-uniform that the catalyst undergoes settling, the hydrogen consumption in the aqueous phase around the settled catalyst is increased too much, thereby lowering the hydrogen concentration of the aqueous phase around the settled catalyst. In a portion of the aqueous phase where the hydrogen concentration is low, the adsorption of hydrogen on the surface of the catalyst is decreased, so that the selectivity for cyclohexene is lowered. It is believed that when the adsorption of hydrogen on the surface of the catalyst is decreased, cyclohexene which is formed on the surface of the catalyst cannot be easily liberated therefrom due to the presence of a large surface area of the catalyst where there is no hydrogen adsorbed, so that conversion of cyclohexene to cyclohexane is more likely to occur.

Examples of monocyclic aromatic hydrocarbons to be used in the present invention as a raw material include benzene, toluene, xylene and lower alkyl benzene having an alkyl group having 4 or less carbon atoms.

The purity of the monocyclic aromatic hydrocarbon as a raw material is desired to be as high as possible. However, the monocyclic aromatic hydrocarbon may contain, as impurities, other hydrocarbon compounds, for example, naphthenes, such as cyclohexane and cyclopentane; paraffins, such as pentane and hexane; and olefins, such as cyclohexene and methylcyclohexene. The raw material may also contain, as impurities, inorganic substances, such as nitrogen and argon.

The purity of the hydrogen gas to be used in the present invention is desired to be as high as possible. However, the hydrogen gas may contain impurities, such as those hydrocarbon compounds and inorganic substances which are described above in connection with the monocyclic aromatic hydrocarbon.

The particulate hydrogenation catalyst to be used in the present invention is comprised mainly of metallic ruthenium. The average crystallite diameter of the catalyst is preferably about 200 Å or less. The catalyst can be obtained by the reduction of various ruthenium compounds. The catalyst may contain other metal values, such as zinc, chrome, molybdenum, tungsten, manganese, cobalt, nickel, iron and copper values, which have been added thereto during or after the preparation of the catalyst. The ruthenium compounds to be used for producing the catalyst are not particularly limited. Examples of employable ruthenium compounds include ruthenium chloride, ruthenium bromide, ruthenium iodide, ruthenium nitrate, ruthenium sulfate, ruthenium hydroxide, ruthenium oxide, ruthenium red, and various ruthenium-containing complexes. The reduction of a ruthenium compound can be performed by a method using hydrogen or a chemical reduction method using a reducing agent, such as formalin, sodium boron hydride and hydrazine. Especially preferred for producing the catalyst is a method in which a ruthenium salt is hydrolyzed to obtain ruthenium hydroxide and the ruthenium hydroxide is then subjected to treatment for reduction.

In the method of the present invention, a catalyst obtained by the reduction of a mixture of a ruthenium compound with a zinc compound is useful for further improving the yield of a cycloolefin. Such a catalyst can be obtained by mixing a valence-having ruthenium compound with a zinc compound and subjecting the mixture to treatment for reduction, thereby reducing the ruthenium compound to a metallic state. Examples of employable valence-having ruthenium compounds include salts, such as ruthenium chloride, ruthenium nitrate and ruthenium sulfate; ruthenium-containing complexes, such as ammine complex salt of ruthenium; ruthenium hydroxide; and ruthenium oxide. Trivalent or tetravalent ruthenium compounds are especially preferred from the viewpoint of availability and ease in handling. On the other hand, zinc compounds employable for producing the catalyst can be selected from a wide variety of zinc compounds. Examples of employable zinc compounds include salts, such as zinc chloride, zinc nitrate and zinc sulfate; zinc complexes, such as ammine complex salt of zinc; zinc hydroxide; and zinc oxide.

The zinc content of the above-mentioned hydrogenation catalyst is generally in the range of from 0.1 to 50% by weight, preferably from 2 to 20% by weight, based on the weight of the ruthenium contained in the hydrogenation catalyst.

Compounds of a ruthenium having a valency which contain zinc may be obtained in the form of a solid or a homogeneous solution. Such a solid may be obtained for example, by a process in which a solution of a ruthenium compound and a zinc compound is first prepared and the solution is subjected to co-precipitation by the conventional technique to thereby obtain a solid.

Such compounds of a ruthenium having a valency which contain zinc can be reduced according to various methods known in the art. For example, the compounds may preferably be reduced according to a method in which a reduction with hydrogen is carried out in a gaseous phase or a method in which a reduction is performed with hydrogen or other reducing agents, such as NaBH$_4$ or formaldehyde, in a liquid phase. It is especially preferred that the reduction be performed with hydrogen in a gaseous or liquid phase.

When a reduction with hydrogen is performed in a gaseous phase, it is generally preferred to avoid an extremely large temperature increase and to dilute the hydrogen with an inert gas, for inhibiting an increase of the crystallite size of ruthenium. On the other hand, when a reduction with hydrogen is performed in a liquid phase, a solid compound of a ruthenium having a valency which contains zinc may either be dispersed in water or an alcohol or may be dissolved therein to obtain a homogeneous solution, prior to reaction for the reduction. The liquid phase is preferably agitated and/or heated to effectively advance the reduction reaction. In place of water, use can be made of an alkali aqueous solution or an aqueous solution of a metal salt, e.g., an alkali metal salt.

The particulate catalyst for hydrogenation as described above is present in a reaction system in the form of crystallites composed mainly of ruthenium and/or particles composed of an agglomerate of such crystallites. The average diameter of such crystallites is generally up to about 200 Å, but preferably up to 150 Å, and more preferably up to about 100 Å, for increasing the selectivity for and yield of a desired cycloolefin and for increasing the reaction rate of hydrogenation. The smaller the particle diameter, the greater the catalytic effect of the catalyst. Generally, however, from a practical viewpoint, there is a preferable lower limit defined by crystallinity. Crystallinity means a symmetrical, regular, periodic arrangement of atoms, for which an X-ray diffraction is observed. The above-mentioned average diameter of crystallites can be determined by the conventional method in which a breadth of diffraction line is measured by X-ray diffractometry and the average diameter is calculated from the breadth of diffraction line according to the Sherrer's equation. In particular, when CuKα rays are employed as an X-ray source, the average diameter of crystallites is calculated from the breadth of diffraction line having a maximum at a diffraction angle (2θ) of about 44°.

In the present invention, the particulate catalyst for hydrogenation can be used as such, or can be used in the form of a composite having a catalyst carried on a carrier, such as aluminosilicate and titanium oxide. In addition to the above described particulate catalyst for hydrogenation, at least one member selected from the group consisting of zirconium oxide and hafnium oxide can be added to a reaction system containing water prior to the initiation of hydrogenation reaction. The amount of these oxides is generally in the range of from $1 \times 10^{-3}$ to 0.3 part by weight, preferably from $1 \times 10^{-2}$ to 0.1 part by weight, per one part by weight of water which is present in the reaction system.

It is preferred that the above oxides added in the present invention be finely particulate, and it is especially preferred that the average particle diameter of the oxides be in the range of from 0.005 to 10 μm (see U.S. Pat. No. 4,734,536).

Further, an alcohol may be added to the reaction system (see Japanese Patent Application Laid-Open Specification No. 61-44830).

Still further, in addition to the hydrogenation catalyst, at least one member selected from the group consisting of oxides of aluminum, gallium, niobium, tantalum, chromium, iron, cobalt, titanium and silicon (see Japanese Patent Application Laid-Open Specification No. 62-201830) may be added to the reaction system prior to the hydrogenation reaction.

Still further, the hydrogenation reaction may be carried out in a slurry of a hydrogenation catalyst as mentioned above in which at least one water-soluble zinc compound (see U.S. Pat. No. 4,734,536) is contained or in which zinc sulfate as a solid base and/or a solid basic salt of zinc sulfate is contained, under either neutral or acidic conditions (see U.S. Pat. No. 4,734,536, and Japanese Patent Application Laid-Open Specification Nos. 63-63627, 63-88139 and 63-152333).

The weight ratio of the hydrogenation catalyst to water present in a reaction system is preferably in the range of from about 0.001 to about 0.2, more preferably from about 0.002 to about 0.15. When the amount of the hydrogenation catalyst is smaller than the lower limit, the rate of hydrogenation reaction is likely to be low to an extent such that an extremely large reactor vessel is required, thereby adversely affecting commercial production. On the other hand, when the amount of the hydrogenation catalyst is larger than the upper limit, the viscosity of the aqueous phase is likely to be so high as to cause the fluidity of the aqueous phase to be lost, thereby adversely affecting the diffusion rate of hydrogen and a monocyclic aromatic hydrocarbon in the aqueous phase. The thus adversely affected diffusion rate leads to a lowering of the rate of hydrogenation reaction.

The hydrogenation reaction is generally performed at a temperature of from about 25° to about 250° C., preferably from about 100° to about 200° C. The hydrogen partial pressure of a hydrogen gas is generally in the range of from about 5 to about 150 kg/cm$^2$, preferably from about 10 to about 100 kg/cm$^2$. When a reactor provided with an agitator is used for the reaction, the hydrogenation reaction is generally performed for a period of from about 5 minutes to about 2 hours. On the other hand, when a reactor tube is used for the reaction, the hydrogenation reaction is generally performed for a period of from about 1 minute to about 20 minutes. Each of these periods of time is defined as a contact time during which a monocyclic aromatic hydrocarbon is in contact with hydrogen gas and the catalyst so that the partial hydrogenation reaction of the monocyclic aromatic hydrocarbon occurs.

In the method of the present invention, hydrogenation reaction is carried out with the aqueous phase present being held under either neutral or acidic conditions. If the aqueous phase becomes alkaline, the rate of reaction will be decreased to an undesirably low level. The pH of the aqueous phase should generally be within the range of from 0.5 to 7, preferably from 0.5 to less than 7, and more preferably from 1 to 6.5.

The isolation of a produced cycloolefin from the oil phase can be conducted as follows.

The oil phase after the partial hydrogenation reaction contains a cycloolefin, a naphthene and an unreacted monocyclic aromatic hydrocarbon. For example, when benzene is used as a starting material, the oil phase after the partial hydrogenation reaction contains cyclohexene as a desired product, cyclohexane as a by-product, and unreacted benzene. The boiling points of cyclohexene, cyclohexane and benzene are very close (83.0° C., 80.8° C. and 80.1° C., respectively) and, therefore, it is difficult to isolate cyclohexene alone from the oil phase by simple distillation. Therefore, extractive distillation can advantageously be used for isolating the cyclohexene. In extractive distillation, distillation is performed in the presence of an appropriate solvent, such as adiponitrile, sulfolane, dimethylacetamide and the like. In extractive distillation, due to the difference in affinity with the solvent between cyclohexene, cyclohexane and unreacted benzene, the relative volatility of the cyclohexene becomes high. More specifically, the relative volatilities of cyclohexene and cyclohexane are, respectively, 1.5 to 3 and 2 to 6, taken relative to the volatility of benzene. Therefore, cyclohexene can be isolated by first separating the cyclohexene and the cyclohexane from the unreacted benzene and then, separating the cyclohexene from the cyclohexane. Alternatively, cyclohexene can be isolated by first separating the unreacted benzene and the cyclohexene from the cyclohexane and then, separating the cyclohexene from the unreacted benzene. In this manner, the produced cyclohexene can be readily isolated. As mentioned above, by extractive distillation, cyclohexane and benzene can be separated from each other, so that the benzene may be used again as a starting material and the cyclohexane may be used for other useful purposes.

Extractive distillation is described in Japanese Patent Application Laid-Open Specification No. 58-164524 (in which dimethylacetamide is used as the solvent), Japanese Patent Application Laid-Open Specification No. 57-47628 (in which a sulfonic compound is used as the solvent), Japanese Patent Application Laid-Open Specification No. 57-55129 (in which an aliphatic dinitrile compound is used as the solvent), and Japanese Patent Application Laid-Open Specification No. 1-135730 (in which a mixed solvent of dimethylacetamide and adiponitrile is used as the solvent).

With reference to FIGS. 1 to 5, several modes of the method of the present invention for performing the partial hydrogenation of a monocyclic aromatic hydrocarbon are described hereinbelow, which, however, should not be construed as limiting the present invention.

In FIG. 1, there is shown a diagrammatic view illustrating one mode of the method of the present invention, in which a reactor is shown in cross-section to show the interior thereof. Reactor 4 is equipped with an agitator, a thermometer protecting sheath (not shown), a common pipe for feeding an oil phase containing the monocyclic aromatic hydrocarbon which is fed through pipe 1 and for introducing water which is fed through pipe 2, pipe 3 for feeding a gaseous phase comprising hydrogen gas, a product outlet for withdrawing a produced cyclohexene through pipe 5, and a pressure gauge (not shown). The reactor has weir 6 extending from above a gas-liquid free surface to below the free surface in the reactor around the product outlet for providing a stationary zone to facilitate separation between an oil phase and an aqueous phase. Further, the reactor has an external electric heater (not shown) for regulation of the reactor temperature. Pipes 1 to 3 have their respective flowmeters (not shown). The product outlet (which is connected to pipe 5) is disposed in the upper portion of the reactor. For observing a state of separation between the oil phase and the aqueous phase in the stationary zone and measuring the oil phase-aqueous phase interface level, the reactor has a glass-made peep window (not shown) in the side wall.

That is, according to this mode of the method of the present invention, the reaction is conducted in a reactor having an agitator with a plurality of agitating blades for applying a shearing force to the reaction system at a maximum shear rate of between about 50 and about 2000/sec, so that the oil phase and the gaseous phase are dispersed in the continuous aqueous phase as globules and as bubbles, respectively. When the agitator is operated, the entire reaction system is agitated to prevent the catalyst suspended in the continuous aqueous phase from settling and to divide aggregated gas bubbles and aggregated oil globules, formed in the reaction system at places distant from the agitating blades, into re-dispersed gas bubbles and re-dispersed oil globules, so that the dispersion of the gas phase as bubbles and the oil phase as globules in the continuous aqueous phase is maintained.

The morphology of reactor 4 is not particularly limited, and it may be of a vertical type or a horizontal type and may be in the form of a rectangular parallelopiped or a cylinder. However, it is generally desired to avoid accumulation of slurry and stagnation of liquid, and from this viewpoint, the most preferred morphology of the reactor is a vertical cylinder.

Agitating blades 7 of the agitator may preferably be of a turbine blade type, a propeller type or a paddle type. Particularly preferred is a turbine blade because in the practice of the method of the present invention, a gas dispersion is most important. The axis of the agitator is not necessarily disposed in the center of the reactor. Only one agitator may be employed or a plurality of agitators may be employed in the partial hydrogenation method of the present invention.

At least one baffle plate may be vertically disposed in the reactor at a position close to the side wall of the reactor. The longer the baffle plate, the more effectively the reaction system is vertically circulated.

In the method of the present invention, it is preferred that the reaction system be agitated so as to produce downward flow components, so that the gaseous phase comprising hydrogen gas and the oil phase containing a monocyclic aromatic hydrocarbon can be circulated in the form of a mixture with the aqueous phase. Illustratively stated, for mixing the gaseous phase and the oil phase, each of which has a specific gravity smaller than that of the aqueous phase, with the aqueous phase, it is preferred that the agitated reaction system contain downward flow components serving to forcibly move downward both gas bubbles and oil globules which are ascending due to the small specific gravity. The downward flow components may be produced either in the center portion of the reactor, as shown in FIG. 1, or in a portion laterally apart from the center portion.

Nevertheless, the gas bubbles ultimately ascend and reach the gas-liquid free surface and then are released therefrom. For ensuring a sufficient time for the gas bubbles to stay in the reaction system, it is desired that the reactor have a height greater than the inner diameter thereof. The ratio of the depth of the reaction system to the inner diameter of the reactor is preferably at least 1, more preferably in the range of from 1 to 10. When the above-mentioned ratio is large, i.e., more than 10, the shaft of the agitator inevitably needs to be long relative to the inner diameter of the reactor, so that undesired shaft vibration is likely to occur.

Hydrogen gas is preferably fed to the reactor at a lower portion thereof, just below the agitating blades 7, through feed pipe 3, more preferably through feed pipe 3 with a dispersing head so that fed hydrogen gas is dispersed into the aqueous phase therethrough. such a dispersing head has, for example, a large number of through-holes with a diameter of between 1.0 and 50 mm.

Likewise, a monocyclic aromatic hydrocarbon is more preferably fed at a lower portion of the reactor, just below the agitating blades 7, through feed pipe 1 having a dispersing head so that a fed monocyclic aromatic hydrocarbon is dispersed into the aqueous phase. In particular, such a dispersing head is preferably disposed at a position distant from the product outlet. Otherwise, it is likely that the fed monocyclic aromatic hydrocarbon immediately reaches the gas-liquid free surface through the aqueous phase and then is evaporated off from the gas-liquid free surface, so that the reaction yield becomes poor. Such a dispersing head has, for example, a large number of through-holes with a diameter of between 1.0 and 75 mm.

The agitator may have either a single set of agitating blades arranged in a common plane (hereinafter referred to simply as "blade set") or a plurality of blade sets arranged in tiers, which may be structurally identical or different.

In the case of a plurality of blade sets arranged in tiers, the blade sets generally comprise a first blade set disposed at the lowermost position for producing and dispersing gas bubbles and oil globules in a continuous aqueous phase and for mixing the gas bubbles and the oil globules in the entire reaction system.

When the reactor is of a commercial scale, the absorption of the hydrogen gas present above the gas-liquid free surface in the reactor into the reaction system through the free surface is less. Accordingly, it is necessary to purge the hydrogen gas from such a reactor. However, when the hydrogen gas is merely purged for discharge from the reaction system, the discharged gas becomes a loss as much, so that the consumption of the hydrogen gas is increased. Therefore, re-compression of the purged gas and re-feeding of the re-compressed gas to a lower portion of the reactor may be conceived. However, this additionally requires a gas circulating compressor for re-compression, thereby causing the reaction apparatus to be complicated. In this situation, the present inventors have made extensive and intensive studies with a view toward rendering unnecessary a gas circulating compressor by re-adsorbing the hydrogen gas present above the gas-liquid free surface in the reactor into the reaction system through the gas-liquid free surface. As a result, it has been found that it is desirable to arrange a plurality of blade sets in tiers, which include a blade set (herein referred to as "second blade set") disposed at a position such that when the agitator is operated, the gas present above the gas-liquid free surface in the reactor is caused to be engulfed into the reaction system below the free surface by the action of the blade set. The above-mentioned position depends upon the structure of agitating blades and the agitating force applied. The second blade set waves the gas-liquid free surface so as for the area of the free surface to be increased, thereby rendering it possible to engulf the gas present above the gas-liquid free surface in the reactor into the reaction system below the free surface. It is generally preferred that the second blade set be disposed within about 1 m below the gas-liquid free surface. Further, it is generally preferred that a draft tube be disposed around the agitator, which promotes the engulfing of the hydrogen gas into the reaction system through the gas-liquid free surface. The above-mentioned draft tube is one of the cavitators known in the art.

The separation of the oil phase from the aqueous phase to thereby take out only the oil phase containing a produced cycloolefin, can be attained by disposing weir 6 around the product outlet (which is connected to pipe 5) for a produced cycloolefin so that a stationary zone to facilitate phase separation is provided, as shown in FIG. 1. That is, when the reaction mixture is allowed to stand still in the stationary zone, the oil globules are caused to ascend, to thereby form a continuous oil phase as an upper layer and a continuous aqueous phase as a lower layer in the stationary zone. Then, the continuous oil phase is withdrawn through outlet pipe 5 and a cycloolefin is then isolated from the oil phase. On the other hand, the continuous aqueous phase separated from the oil phase descends due to its specific gravity which is higher than the reaction mixture, so that the separated continuous aqueous phase is replaced with the reaction mixture. The reaction mixture is then separated into the oil phase and the aqueous phase as mentioned above.

Figure 5:
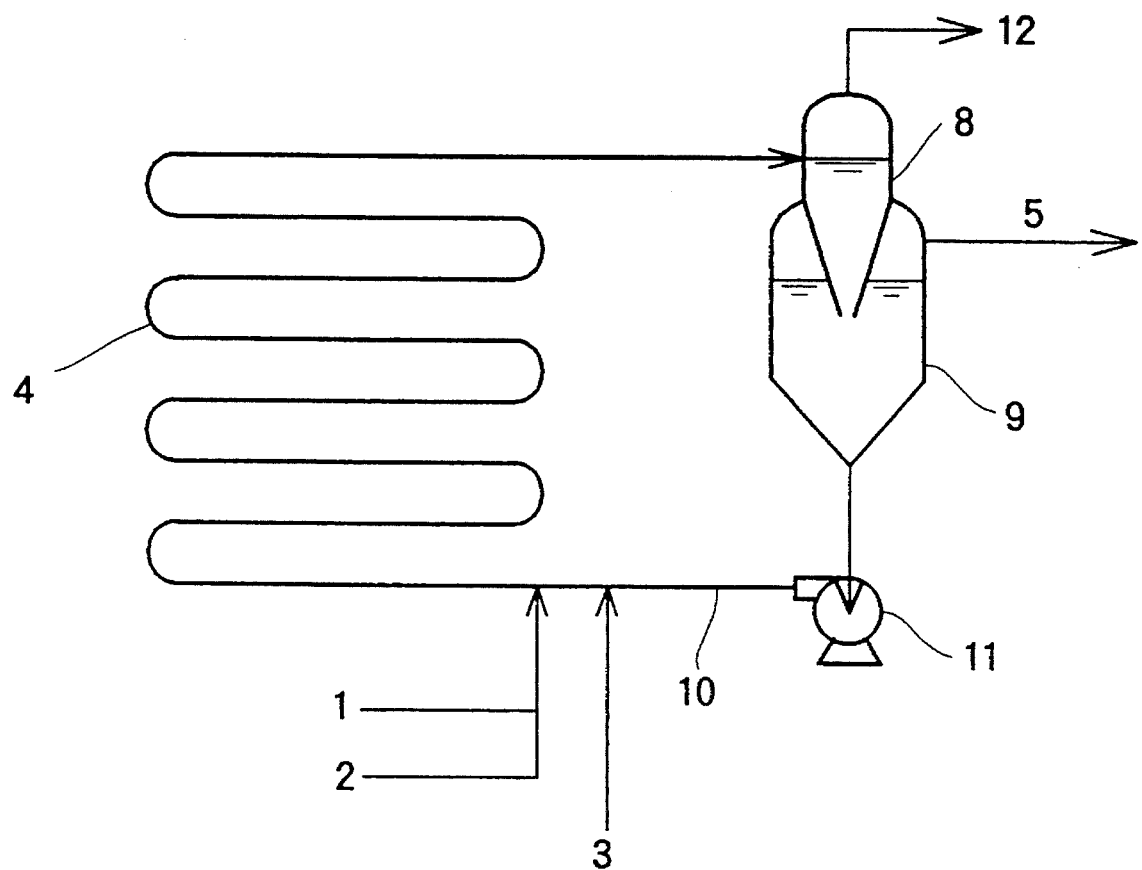
FIG. 5 is a diagrammatic view illustrating a further mode of the method of the present invention utilizing a reactor tube.

As an alternative method for separating the oil phase from the aqueous phase, there is a method in which a reaction mixture obtained by the reaction and comprising a gas comprised of hydrogen gas and a liquid comprised of an oil phase and an aqueous phase, is introduced to a gas-liquid separator (not shown in FIG. 1) disposed outside of the reactor to effect separation between the gas and the liquid, and the liquid is introduced to an oil phase-aqueous phase separator (disposed outside of the reactor) to thereby separate the oil phase as an upper layer containing a produced cycloolefin from the aqueous phase as a lower layer comprising the water and the particulate hydrogenation catalyst suspended therein, followed by withdrawal of the upper layer of oil phase while recycling the lower layer of aqueous phase to the reactor by the use of a pump or by gravity. As the gas-liquid separator and oil phase-aqueous phase separator disposed outside of the reactor, which are not shown in FIG. 1, for example, the same gas-liquid separator 8 and oil phase-aqueous phase separator 9 as shown in FIGS. 2, 3 and 5 can be employed.

Referring back to FIG. 1, in separating the oil phase from the aqueous phase in the stationary zone provided in the reactor with weir 6, when bubbles of hydrogen gas are present in the stationary zone, the bubbles and the catalyst entrained thereby ascend from the aqueous phase into the continuous oil phase, so that the catalyst will leak out when the reaction product (oil phase) is withdrawn from the stationary zone. For preventing bubbles from entering the stationary zone, it is desirable to provide barrier 13 near the inlet of the stationary zone, as shown in FIG. 1. Further, when a gas-liquid separator and an oil phase-aqueous phase separator are provided outside of the reactor as described above, it is desirable that the liquid introduced from the gas-liquid separator to the oil phase-aqueous phase separator contain no bubbles. From the viewpoint of assuring complete separation between the gas and the liquid, it is preferred that the gas-liquid separator contain a portion like a downcomer in the conventional sieve tray type distilling tower so that the liquid is gently fed to the oil phase-aqueous phase separator without occurrence of bubbles. From this viewpoint, the gas-liquid separator is desired to have such a structure as that of gas-liquid separator 8 of FIGS. 2, 3 and 5.

According to another mode (second mode) of the method of the present invention, a partial hydrogenation reaction is conducted using a plurality of reactors connected in series and comprising a first reactor and at least one additional reactor. A reaction mixture, which is obtained in a reactor preceding said additional reactor and comprises a produced cycloolefin and an unreacted monocyclic aromatic hydrocarbon, is introduced to the additional reactor to thereby partially hydrogenate the unreacted monocyclic aromatic hydrocarbon.

Figure 2:
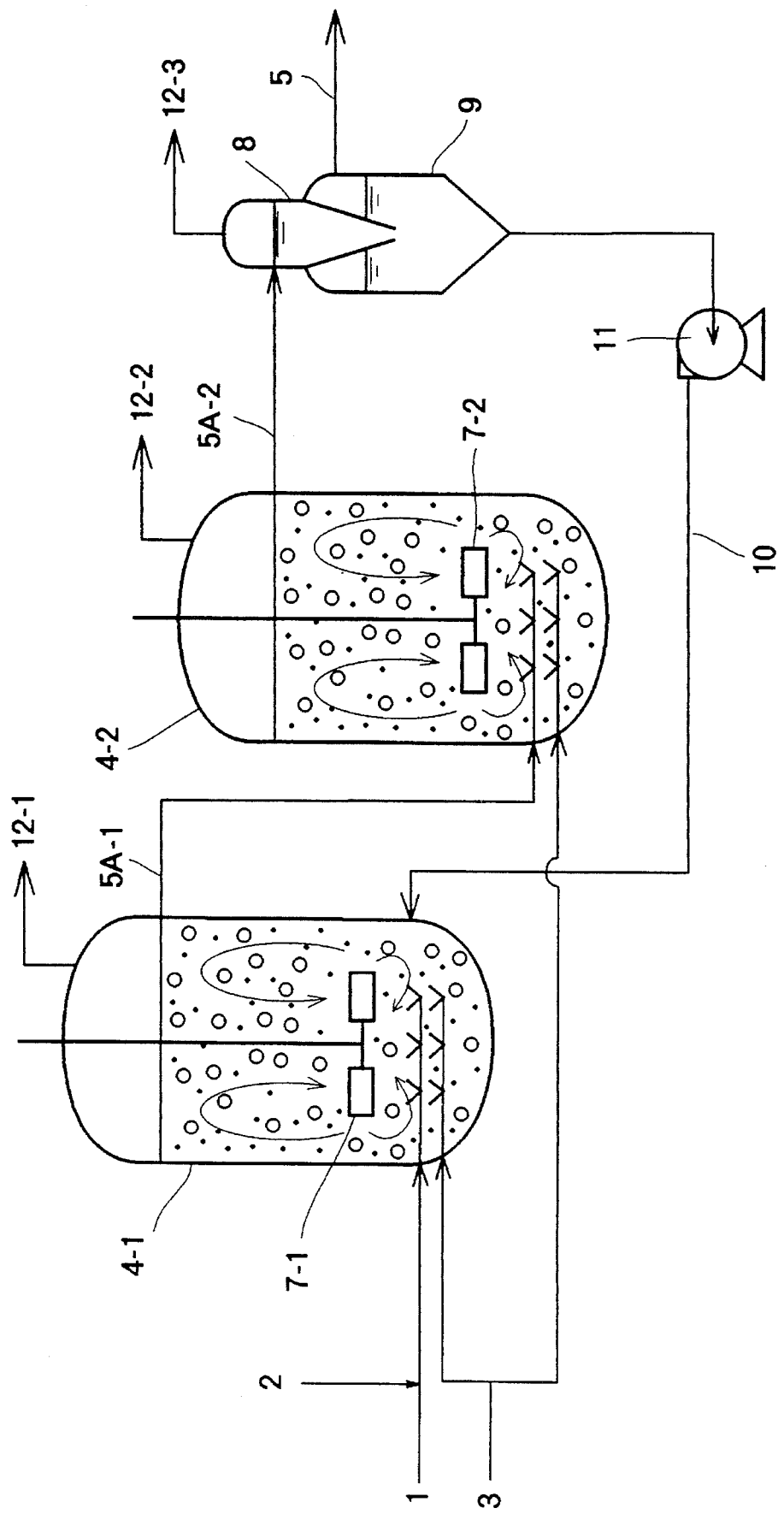
FIG. 2 is a diagrammatic view illustrating another mode of the method of the present invention utilizing two reactors connected in series.
Figure 3:
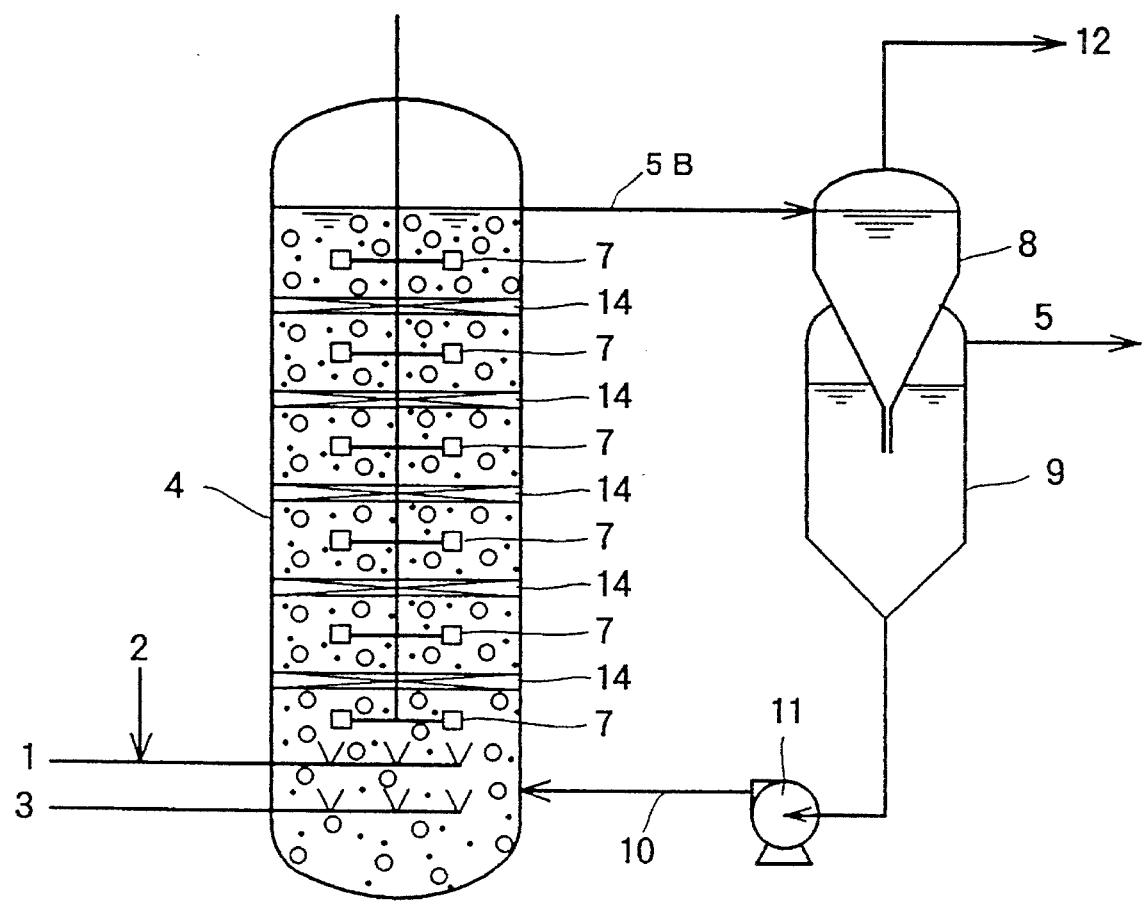
FIG. 3 is a diagrammatic view illustrating still another mode of the method of the present invention utilizing a reactor having an agitator with a plurality of blade sets arranged in tiers, the reactor being partitioned by means of baffle means into a plurality of chambers each containing at least one set of the blade sets.

FIG. 2 shows a diagrammatic view illustrating the second mode of the method of the present invention utilizing two reactors connected in series. First reactor 4-1 is equipped with an agitator, a thermometer protecting sheath (not shown), a common pipe for feeding an oil phase containing the monocyclic aromatic hydrocarbon which is fed through pipe 1 and for introducing water which is fed through pipe 2, pipe 3 for feeding a gaseous phase comprising hydrogen gas, outlet pipe 5A-1 for a reaction mixture obtained in first reactor 4-1, and a pressure gauge (not shown). The reactor has an external electric heater (not shown) for regulation of the reaction temperature. Pipes 1 to 3 have their respective flowmeters (not shown). Outlet pipe 5A-1 is connected to an upper portion of reactor 4-1. For observing the internal state of the reactor, the reactor has a glass-made peep window (not shown) in the side wall. The gas is discharged from reactor 4-1 through hydrogen gas discharge pipe 12-1. Outlet pipe 5A-1 is connected to a lower portion of additional reactor 4-2, and pipe 3 for feeding a gaseous phase comprising hydrogen gas is also connected to reactor 4-2 at a portion below the portion to which outlet pipe 5A-1 is connected. A dispersing head (as shown in FIG. 2) connected to the forward end of pipe 5A-1 may be omitted. The gas is discharged from reactor 4-2 through hydrogen gas discharge pipe 12-2. Various other equipments, such as pressure gauge and the like, are of the same types as those employed in reactor 4-1. Outlet pipe 5A-2 of reactor 4-2 is connected to gas-liquid separator 8 so as for a reaction mixture obtained in reactor 4-2 to be fed into gas-liquid separator 8. In gas-liquid separator 8, a gas comprised of hydrogen gas is separated from a liquid comprised of an oil phase and an aqueous phase. The gas is discharged through hydrogen gas discharge pipe 12-3. Gas-liquid separator 8 communicates, at its lower portion, to an upper portion of oil phase-aqueous phase separator 9 so as for the liquid to be introduced into oil phase-aqueous phase separator 9. In oil phase-aqueous phase separator 9, the liquid is separated into an upper layer of oil phase, which contains a produced cyclohexene, and a lower layer of aqueous phase, which is comprised of the water and the hydrogenation catalyst suspended therein. The oil phase is withdrawn through oil phase outlet pipe 5. On the other hand, the aqueous phase is withdrawn through an aqueous phase outlet pipe provided at the lowermost portion of oil phase-aqueous phase separator 9, and recycled through circulation pipe 10 to the inlet of first reactor 4-1 by means of pump 11. All the pipes have their respective flowmeters.

Use of such a plurality of reactors in which the reaction mixture moves as a piston flow can increase the selectivity for a cycloolefin. The reason is that, in the method of the present invention in which the desired product is an intermediate reaction product of a successive reaction, when the reaction mixture moves as a piston flow through a plurality of reactors, the concentration of a monocyclic aromatic hydrocarbon can be maintained at a maximum level, thereby facilitating the formation of a cycloolefin while holding down further conversion of the cycloolefin to a cycloparaffin as a by-product.

The effect of the above-mentioned second mode of the method of the present invention using a plurality of reactors connected in series can also be achieved by a reactor which is partitioned by means of baffle means into a plurality of chambers arranged in tiers so that each chamber contains at least one set of the blade sets. An example of such a reactor is shown in FIG. 3.

Accordingly, in still another mode (third mode) of the method of the present invention, as shown in FIG. 3, the reaction is conducted in a reactor 4 having an agitator with a plurality of agitating blades 7 for producing the shearing force, the plurality of agitating blades 7 including a plurality of blade sets arranged in tiers, wherein the reactor 4 is partitioned by means of baffle means 14 into a plurality of chambers arranged in tiers so that each chamber contains at least one set of the blade sets.

In the third mode of the method of the present invention, the entire reaction system in each chamber is agitated by means of the agitator provided therein to thereby prevent the catalyst suspended in the continuous aqueous phase from settling and to thereby divide aggregated gas bubbles and aggregated oil globules, formed in the reaction system in each chamber at places distant from the agitating blades, into re-dispersed gas bubbles and re-dispersed oil globules, so that the dispersion of the gas phase as bubbles and the oil phase as globules in the continuous aqueous phase in each chamber is maintained.

Baffle means 14 allows the reaction system to flow from a first chamber of two mutually adjacent chambers partitioned by the baffle means to a second chamber of the mutually adjacent chambers in accordance with a predetermined direction of flow of the reaction system. The baffle means prevents flow of the reaction system in a counter direction to the predetermined direction, so that the reaction system in the second chamber is prevented as well as possible from being back-mixed with the reaction system in the first chamber. Thus, each of the chambers partitioned by baffle means 14 can function as a separate reactor having an agitator.

Baffle means 14 is not particularly limited and can be, for example, a porous plate, a net-like structure, a doughnut type plate, a semilunar plate, a grid deck, a cone-shaped angle deck, and a plate which is disposed in the reactor so that a gap is left between the periphery of the plate and the inner wall surface of the reactor. Various types of baffle means may be used individually or in combination.

Figure 4A:
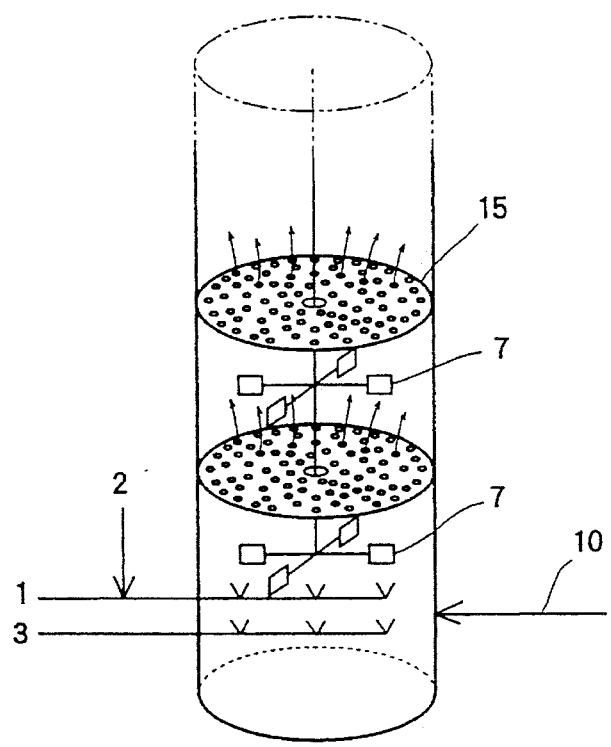
FIGS. 4(a) through 4(c) are diagrammatic views showing various types of baffle means, such as a porous plate [FIG. 4(a)], a doughnut type plate [FIG. 4(b)] and a disc type plate [FIG. 4(c)], which can be used in a reactor shown in FIG. 3 to partition the reactor into a plurality of chambers.
Figure 4B:
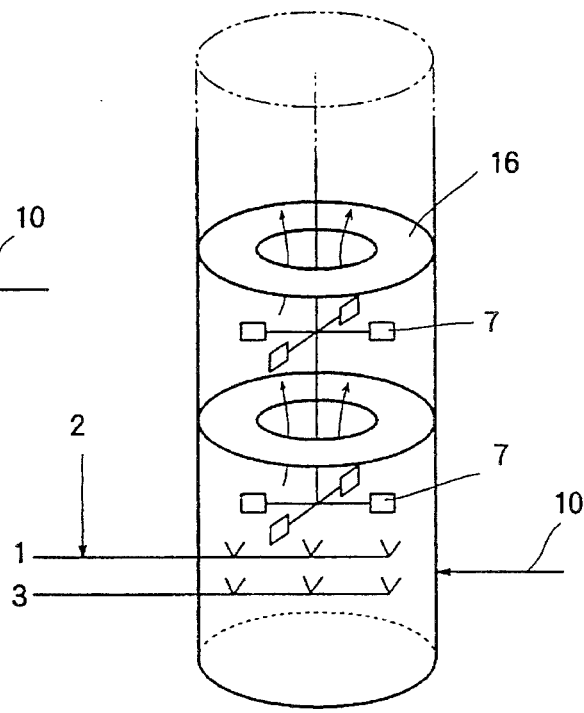
Figure 4C:
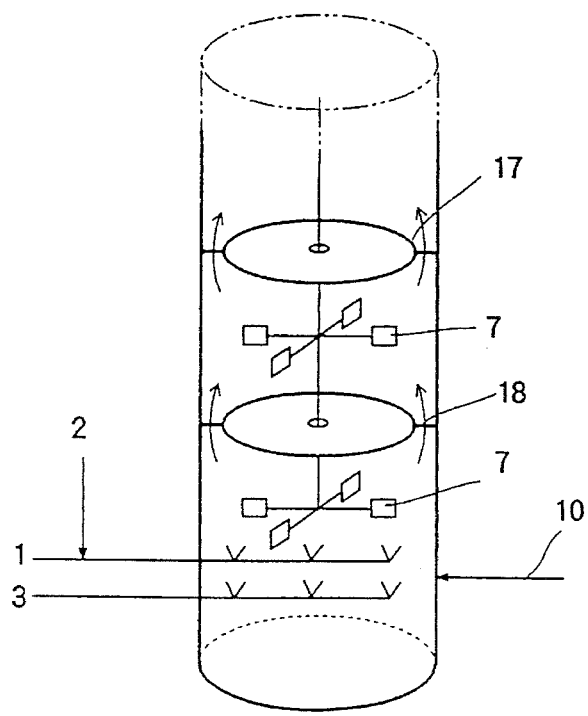

In FIGS. 4(a), 4(b) and 4(c), three types of baffle means are shown. FIG. 4(a) shows an example of baffle means of a porous plate 15, FIG. 4(b) shows another example of baffle means of a doughnut type plate 16, and FIG. 4(c) shows still another example of baffle means of a plate 17 which is disposed in the reactor so that a gap is left between the periphery thereof and the inner wall surface of the reactor. Plate 17 can be fixed to the inner wall surface of the reactor by means of support 18. When baffle means 14 is used, the reaction system is flowed through the baffle means 14 in a direction indicated by arrow in the respective Figure.

The ratio of the height of a chamber (i.e., agitation zone) formed between two adjacent baffle means 14, 14 to the diameter of the reactor is preferably 0.2 to 2. The type of agitation blades 7 may or may not be different between the agitation zones. The position of a blade set in an agitation zone is preferably in the middle of the height of the agitation zone, but the position is not particularly restricted as long as a satisfactory agitation can be attained.

In this third mode of the method of the present invention, it is preferred that the uppermost blade set contained in the uppermost chamber is disposed at a position such that when the agitator is operated, a gas present above a gas-liquid free surface in the reactor is caused to be engulfed into the reaction system below the free surface by the action of the uppermost blade set.

For obtaining a reaction product, instead of providing, outside of reactor 4, a recycling route through a gas-liquid separator and an oil phase-aqueous phase separator as shown in FIG. 3, reactor 4 shown in FIG. 3 may have a product outlet (which is connected to pipe 5B) for a reaction product and have a weir (not shown) around the product outlet for providing a stationary zone to thereby facilitate separation of a reaction mixture obtained by the reaction into an upper oil layer comprising a produced cycloolefin and a lower aqueous layer having the catalyst suspended therein, as shown in FIG. 1. In this case, the product outlet and weir are provided in the uppermost chamber. Also, a barrier for preventing bubbles from entering the stationary zone may be disposed around the inlet of the stationary zone.

Alternatively, as shown in FIG. 3, the reaction mixture obtained by reactor 4, as such, may be introduced to a gas-liquid separator 8 disposed outside of the reactor to effect separation between the gas and the liquid. The liquid is introduced to oil phase-aqueous phase separator 9 to thereby separate the oil phase as an upper layer containing a produced cycloolefin from the aqueous phase as a lower layer comprising the water and the catalyst suspended therein, followed by withdrawal of the oil phase while recycling the aqueous phase to the reactor.

In the third mode of the method of the present invention using a reactor partitioned by means of baffle means, not only does the reaction system assume a piston flow through a plurality of chambers arranged in tiers, thereby improving the reaction yield by one pass through the reactor, but also the gas hold-up can be increased, thereby facilitating the adsorption of hydrogen gas.

Referring to FIG. 5, there is shown a further mode (fourth mode) of the method of the present invention. In this fourth mode, the reaction is performed while circulating the reaction system through reactor tube 4 at a flow rate sufficient to exert the shearing force at a maximum shear rate of between about 50 and about 2000/sec.

In FIG. 5, the oil phase, the aqueous phase and the gaseous phase are, respectively, fed from pipes 1, 2 and 3 into reactor tube 4, through which the reaction system is circulated at a flow rate sufficient to exert the shearing force at the above-mentioned requisite maximum shear rate.

With respect to the shape of reactor tube 4, either a cylindrical shape or a prismatic shape can be employed. It is preferred that the length of reactor tube 4 be satisfactorily large relative to the inner diameter thereof so that a piston flow of the reaction system can be attained. As described above, a piston flow of the reaction system leads to an improvement in the selectivity for a cycloolefin. The reaction system is circulated through reactor tube 4 at a flow rate sufficient to exert the necessary shearing force. When the reaction system is circulated at too high a flow rate, a pressure loss occurring between the inlet and outlet of the reactor tube increases, thereby lowering the concentration of the hydrogen in the aqueous phase in the downstream portion of the reactor tube, which in turn reduces the selectivity for a cycloolefin. Feeding of a hydrogen gas and a monocyclic aromatic hydrocarbon can be performed directly from the respective feed pipes. However, when feeding pipes having a dispersing head with a number of through-holes, formation of oil globules and gas bubbles is facilitated. For facilitating the separation between the oil phase and the aqueous phase after the reaction so as to obtain an oil phase containing a cycloolefin, gas-liquid separator 8 is provided on the side of the outlet of reactor tube 4. That is, a reaction mixture obtained by the reaction and comprising a gas comprised of hydrogen gas and a liquid comprised of an oil phase and an aqueous phase, is introduced to gas-liquid separator 8 disposed outside of reactor tube 4 to effect separation between the gas and the liquid. The gas is withdrawn through pipe 12 and the liquid is introduced to gas phase-aqueous phase separator 9 to thereby separate the oil phase as an upper layer containing a produced cycloolefin from the aqueous phase as a lower layer comprising the water and the particulate hydrogenation catalyst suspended therein, followed by withdrawal of the oil phase as a reaction product through pipe 5 while recycling the aqueous phase to reactor tube 4 by means of, for example, pump 11.

Incidentally, in this fourth mode using a reactor tube, when hydrogen gas is supplied only from pipe 3, the gas hold-up of the reaction system is likely to be insufficient, causing the reaction rate to be limited. In order to increase the gas hold-up of the reaction system, a recycling system for hydrogen gas may be provided in which hydrogen gas withdrawn from gas-liquid separator 8 through pipe 12 is returned to reactor tube 4 through, for example, a circulating compressor, so that a satisfactory quantity of gas bubbles can be supplied.

In this fourth mode of the method of the present invention, the reaction system assumes a piston flow through reactor tube 4 and, hence, the selectivity for a cycloolefin is enhanced, leading to an increase of reaction yield. However, as described above, when a reactor tube is employed, it is frequently needed to use a recycling system for hydrogen gas, thus rendering complicated the reaction apparatus. On the other hand, in the above-mentioned first to third modes of the present invention in which a reactor having an agitator is employed [e.g., FIGS. 1 to 3], the reaction apparatus is considerably simple as compared to that for the fourth mode utilizing a reactor tube. In general, when the merits and demerits of the above modes are taken into consideration, the first to third modes using a reactor having an agitator are more preferred than the fourth mode using a reactor tube.

PREFERRED EMBODIMENT OF THE INVENTION

The present invention will now be described in greater detail with reference to the following Examples and Comparative Examples, which should not be construed as limiting the scope of the present invention.

EXAMPLE 1

As a hydrogenation catalyst, particulate metallic ruthenium having an average crystallite diameter of 55 Å, which has a zinc content of 7.4% by weight, is used.

A partial hydrogenation reaction of benzene is carried out under the following conditions.

As a partial hydrogenation reactor, an autoclave having a capacity of 4 liters is employed. As is diagrammatically shown in FIG. 1, the autoclave having its inner surface coated with Teflon (trademark of a polytetrafluoroethylene resin produced by E.I. Du Pont De Nemours and Company, U.S.A.), is equipped with an agitator, a thermometer protecting sheath (not shown), a common pipe for feeding an oil phase containing benzene which is fed through pipe 1 and for introducing water which is fed through pipe 2, pipe 3 for feeding a gaseous phase comprising hydrogen gas, a product outlet (which is connected to pipe 5) for a produced cyclohexene, and a pressure gauge (not shown). Agitating blades 7 of the agitator are one-step type turbine blades. The autoclave has weir 6 extending from above a gas-liquid free surface to below the free surface in the reactor around the product outlet for providing a stationary zone to facilitate separation between an oil phase and an aqueous phase. Further, the autoclave has an external electric heater for regulation of the autoclave temperature. Pipes 1 to 3 have their respective flowmeters. The product outlet (which is connected to pipe 5) is disposed in the upper portion of the autoclave. For observing a state of separation between the oil phase and the aqueous phase in the stationary zone and measuring the oil phase-aqueous phase interface level, the autoclave has a glass-made peep window in the side wall.

A hydrogenation reaction is carried out according to the procedure mentioned below. First, the inside of the reactor is purged with nitrogen. After purging with nitrogen, 9.8 g of the above-mentioned hydrogenation catalyst, 1.40 liters of water, 248 g of ZnSO$_4$.7H$_2$O and 49 g of powdery ZrO$_2$ having an average particle diameter of 0.35 μm are charged into the reactor. The agitator is operated at 600 rpm to agitate the charged materials, and the inner temperature of the reactor is elevated to and kept at 140° C. by means of the external electric heater. Then, hydrogen gas is introduced under pressure to the reactor and then, a fresh benzene liquid is fed gradually and then at a flow rate of 1.25 kg/hr under steady operation conditions. The internal total pressure of the reactor is maintained at 50 kg/cm$^2$ under steady operation conditions. The level of the oil phase-aqueous phase interface in the stationary zone is adjusted so that the interface is maintained at a level lower than the position of the product outlet (which is connected to pipe 5) for a produced cyclohexene, and water is additionally supplied through pipe 2 in an amount corresponding to the amount of water which is taken away in a dissolved form in a reaction product. The gas-liquid interface (free surface) level is kept constant by adopting an overflow-type pipe as outlet pipe 5. Another peep window is provided in the side wall of the reactor for observing the internal state of the reactor. Observations through the window show that the introduced hydrogen gas is relatively uniformly dispersed as fine bubbles and that the oil phase also is relatively uniformly dispersed as fine oil globules. After the entire reaction system has become steady, the composition of a reaction product withdrawn from outlet pipe 5 is analyzed. The analysis shows that the conversion of benzene is 38%, the selectivity for cyclohexene is 80% and the by-product is cyclohexane. The obtained values are the results of the reaction performed under the reaction rate-limiting conditions, and are found to be satisfactory. Also, the maximum shear rate in this reaction is about 440/sec, and the oil globules have an average diameter of 0.1 mm. The separation of the oil phase from the aqueous phase in the stationary zone is good, with no catalyst observed in the reaction product withdrawn from outlet pipe 5.

In order to measure the time required for separation between the oil phase and the aqueous phase, the feeding of the materials and the agitation of the entire reaction system are simultaneously and temporarily stopped. 23 seconds after stopping the agitation, a continuous oil phase is formed as an upper layer and a continuous aqueous phase as a lower layer. The oil globules present between the two phases have completely disappeared. The volume ratio of the oil phase to the aqueous phase in the reaction system is 0.25.

EXAMPLES 2 AND 3

Using the same reactor as in Example 1, a partial hydrogenation reaction of benzene is carried out under substantially the same reaction conditions as in Example 1, except that the revolution rate of the agitator is varied as indicated in Table shown below. Results are also shown in Table. The obtained values are the results of the reaction performed under the reaction rate-limiting conditions, and are found to be satisfactory. The separation of the oil phase from the aqueous phase in the stationary zone is good, with no catalyst observed in the reaction product withdrawn from outlet pipe 5.

COMPARATIVE EXAMPLE 1

Using the same reactor as in Example 1, a partial hydrogenation reaction is carried out under substantially the same reaction conditions as in Example 1 except that the agitator is operated at 60 rpm instead of 600 rpm. The analysis of the composition of a reaction product withdrawn from outlet pipe 5 shows that the conversion of benzene is 4%, the selectivity for cyclohexene is 45% and the by-product is cyclohexane. The maximum shear rate is 44/sec. With respect to the dispersion state observed during the agitation, it is found that a continuous oil phase is present in the upper layer of the reaction system. That is, the oil phase and the aqueous phase are completely separated, and almost no dispersed oil phase (globules) is observed.

EXAMPLE 4

Example 4-1

Using the same type of hydrogenation catalyst as in Example 1, a partial hydrogenation reaction of benzene is carried out under the following conditions.

As a partial hydrogenation reactor, an autoclave is employed, which is the same type as in Example 1 except that the autoclave has a capacity of 4,000 liters instead of a capacity of 4 liters, and is equipped with an agitator having, as agitating blades 7, two-step type turbine blades instead of one-step type turbine blades. Further, the autoclave has an external jacket for regulation of the autoclave temperature, instead of the external electric heater. Various feeding pipes including pipes 1, 2 and 3, an outlet pipe 5, a pressure gauge, flowmeters, a glass-made peep window and the like are of the same types as those employed in Example 1.

A hydrogenation reaction is carried out according to the procedure as follows. First, the inside of the reactor is purged with nitrogen. After purging with nitrogen, 14.7 kg of the above-mentioned hydrogenation catalyst, 2,100 liters of water, 372 kg of ZnSO$_4$.7H$_2$O, and 74 kg of powdery ZrO$_2$ having an average particle diameter of 0.35 μm are charged into the reactor. The agitator is operated at 108 rpm to agitate the charged materials, and steam is introduced into the jacket attached to the autoclave to elevate the inner temperature of the reactor to 140° C. Then, hydrogen gas is introduced under pressure to the reactor and then, a fresh benzene liquid is fed gradually and then at a flow rate of 1,870 kg/hr under steady operation conditions. After the start of the reaction, water for cooling is introduced into the jacket so that the autoclave inner temperature is adjusted to 140° C. The internal total pressure of the reactor is maintained at 50 kg/cm$^2$ under steady operation conditions. The level of the oil phase-aqueous phase interface in the stationary zone is adjusted so that the interface is maintained at a level lower than the position of the product outlet (which is connected to pipe 5) for a produced cyclohexene, and water is additionally supplied through pipe 2 in an amount corresponding to the amount of water which is taken away in a dissolved form in a reaction product. The gas-liquid interface (free surface) level is kept constant by adopting an overflow-type pipe as outlet pipe 5. The internal state of the reactor is observed through a peep window provided in the side wall of the reactor. Observations through the window show that the introduced hydrogen gas is relatively uniformly dispersed as fine bubbles and that an oil phase also is relatively uniformly dispersed as fine oil globules. It is assumed that the gas bubbles have an average diameter of about 2 mm. The reactor is operated under conditions such that purging of hydrogen gas from discharging pipe 12 is zero. After the entire reaction system has become steady, the composition of a reaction product withdrawn from outlet pipe 5 is analyzed. The analysis shows that the conversion of benzene is 39%, the selectivity for cyclohexene is 80% and the by-product is cyclohexane. The obtained values are the results of the reaction performed under the reaction rate-limiting conditions, and are found to be satisfactory. Also, the maximum shear rate in this reaction is about 860/sec, and the oil globules have an average diameter of 0.2 mm. The separation of the oil phase from the aqueous phase in the stationary zone is good, with no catalyst observed in the reaction product withdrawn from outlet pipe 5.

In order to measure the time required for separation between the oil phase and the aqueous phase, the feeding of the materials and the agitation of the reaction system are simultaneously and temporarily stopped. 5 minutes after stopping the agitation, a continuous oil phase is formed as an upper layer and a continuous aqueous phase as a lower layer. The oil globules present between the two phases have completely disappeared. The volume ratio of the oil phase to the aqueous phase in the reaction system is 0.3, and the hold-up of the gaseous phase is 0.03 in the reaction system.

Example 4-2

Figure 6:
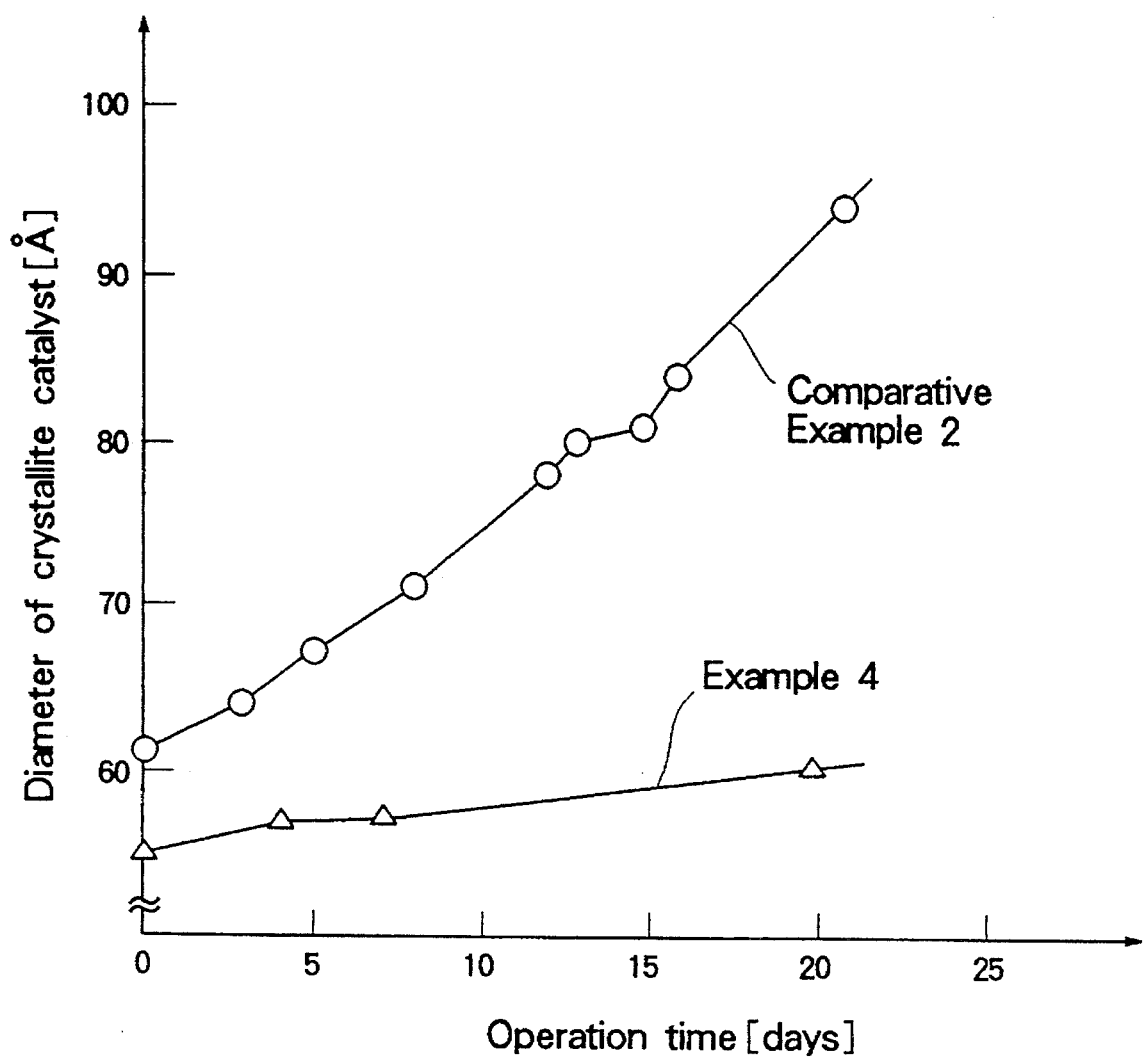
FIG. 6 is a graph showing the change of the average crystallite diameter of a crystallite hydrogenation catalyst vs. the operation time, with respect to Example 4 and Comparative Example 2 described herein.

After measuring the time required for separation between the oil phase and the aqueous phase in the stationary zone, the partial hydrogenation reaction is restarted and continued for 20 days under substantially the same reaction conditions as in Example 4-1, while occasionally measuring the average crystallite diameter of the particulate hydrogenation catalyst. 20 days after the restart, the change of the average crystallite diameter of the particulate hydrogenation catalyst with time which diameter represents a catalytic activity, is evaluated. Results are shown in FIG. 6 (see the curve of Example 4). As shown in FIG. 6, it is found that the increase in the average crystallite diameter of the catalyst with time is very small and the catalytic activity is stable. The analysis of the composition of a reaction product withdrawn from outlet pipe 5 after 20 days from the restart shows that the conversion of benzene is 38%, the selectivity for cyclohexene is 81% and the by-product is cyclohexane. Almost no lowering of the catalytic activity is observed. The separation of the oil phase from the aqueous phase in the stationary zone is good, with no catalyst observed in the reaction product withdrawn from outlet pipe 5.

COMPARATIVE EXAMPLE 2

Comparative Example 2-1

Using the same reactor as in Example 4, a partial hydrogenation reaction is carried out under substantially the same reaction conditions as in Example 4 except that the agitator is operated at 200 rpm. After the entire reaction system has become steady, the composition of a reaction product withdrawn from outlet pipe 5 is analyzed. The analysis shows that the conversion of benzene is 38%, the selectivity for cyclohexene is 81% and the by-product is cyclohexane. The average crystallite diameter of the hydrogenation catalyst is 61 Å, and the oil globules have an average diameter of 0.015 mm.

In order to measure the time required for separation between the oil phase and the aqueous phase, the feeding of the materials and the agitation of the entire reaction system are simultaneously and temporarily stopped. As a result, it is found that, even a time as long as 10 minutes after stopping the agitation, a part of the oil phase has remained in the form of globules.

Comparative Example 2-2

The reaction of Comparative Example 2-1 is continued for 22 days under substantially the same reaction conditions as in Comparative Example 2-1, while occasionally measuring the average crystallite diameter of the particulate hydrogenation catalyst. After completion of the reaction, the change of the crystallite diameter of the hydrogenation catalyst with time is evaluated. Results are shown in FIG. 6 (see the curve of Comparative Example 2). The composition of a reaction product withdrawn from outlet pipe 5 is analyzed. The analysis shows that the conversion of benzene is 24%, the selectivity for cyclohexene is 79% and the by-product is cyclohexane. The maximum shear rate is 2,200/sec. As is apparent from the above, the catalytic activity has remarkably lowered with time.

EXAMPLE 5

Using the same reactor as in Example 4 except that the agitator is equipped with two-step type propeller blades instead of two-step type turbine blades, a partial hydrogenation reaction of benzene is carried out under substantially the same reaction conditions as in Example 4 except that the agitator is operated at 45 rpm instead of 108 rpm, the inner temperature of the reactor is adjusted to 150° C. instead of 140° C., and the internal total pressure of the reactor is maintained at 70 kg/cm$^2$ instead of 50 kg/cm$^2$ under steady operation conditions. A fresh benzene liquid is fed at a flow rate of 1,870 kg/hr under steady operation conditions.

After the entire reaction system has become steady, observations through a peep window formed in the side wall of the reactor are made. As a result, it is found that the introduced hydrogen gas is relatively uniformly dispersed as fine bubbles and that the oil phase also is relatively uniformly dispersed as fine oil globules. It is found that the gas bubbles have an average diameter of about 13 mm and that the oil globules have an average diameter of about 24 mm. The analysis of the composition of a reaction product withdrawn from outlet pipe 5 shows that the conversion of benzene is 37%, the selectivity for cyclohexene is 78% and the by-product is cyclohexane. The obtained values are almost the results of the reaction performed under the reaction rate-limiting conditions, and are found to be satisfactory. Also, the maximum shear rate in this reaction is about 70/sec. The separation of the oil phase from the aqueous phase in the stationary zone is good, with no catalyst observed in the reaction product withdrawn from outlet pipe 5.

EXAMPLE 6

Example 6-1

Using the same reactor as in Example 4, a partial hydrogenation reaction of benzene is carried out under substantially the same reaction conditions as in Example 4 except that the agitator is operated at 175 rpm instead of 108 rpm, the inner temperature of the reactor is adjusted to 125° C. instead of 140° C. and the internal total pressure of the reactor is maintained at 45 kg/cm$^2$ instead of 50 kg/cm$^2$ under steady operation conditions.

After the entire reaction system has become steady, observations through a peep window formed in the side wall of the reactor are made. As a result, it is found that the introduced hydrogen gas is relatively uniformly dispersed as fine bubbles and that the oil phase also is relatively uniformly dispersed as fine oil globules. It is found that the gas bubbles have an average diameter of about 0.6 mm and that the oil globules have an average diameter of about 0.04 mm. The analysis of the composition of a reaction product withdrawn from outlet pipe 5 shows that the conversion of benzene is 32%, the selectivity for cyclohexene is 82%, and the by-product is cyclohexane. The hydrogenation catalyst has an average crystallite diameter of 56 Å. The obtained values are the results of the reaction performed under the reaction rate-limiting conditions, and are found to be satisfactory. Also, the maximum shear rate in this reaction is about 1800/sec. The separation of the oil phase from the aqueous phase in the stationary zone is good, with no catalyst observed in the reaction product withdrawn from outlet pipe 5.

Example 6-2

The reaction of Example 6-1 is continued for 15 days under substantially the same reaction conditions as in Example 6-1. After completion of the reaction, the composition of a reaction product withdrawn from outlet pipe 5 is analyzed. The analysis shows that the conversion of benzene is 30%, the selectivity for cyclohexene is 82%, and the by-product is cyclohexane. The hydrogenation catalyst has an average crystallite diameter of 65 Å. As is apparent from the above, the increase in the crystallite diameter of the hydrogenation catalyst with time is very little and therefore the catalytic activity is stable during the reaction.

EXAMPLE 7

Using the same hydrogenation catalyst as in Example 1, a partial hydrogenation reaction of benzene is carried out under the following conditions.

As a partial hydrogenation reactor, a reactor tube having a capacity of 4,000 liters is employed, which has its inner surface coated with Teflon (trademark of polytetrafluoroethylene manufactured and sold by E.I. Du Pont De Nemours and Company, U.S.A.).

Reactor tube 4 shown in FIG. 5 is used. Reactor tube 4 has at an inlet thereof a thermometer protecting sheath (not shown). Reactor tube 4 is provided with a common pipe for introducing benzene which is fed through pipe 1 and for introducing water which is fed through pipe 2, pipe 3 for feeding hydrogen gas, and a pressure gauge (not shown). Further, reactor tube 4 has, at its outlet also, a thermometer protecting sheath (not shown) and a pressure gauge (not shown). The outlet of reactor tube 4 is fluidtightly connected to gas-liquid separator 8 so as for a reaction mixture produced in reactor tube 4 to be fed into gas-liquid separator 8. In gas-liquid separator 8, a gas comprised of hydrogen gas is separated from a liquid comprised of an oil phase and an aqueous phase. The gas is discharged through hydrogen gas discharge pipe 12. Gas-liquid separator 8 is fluidtightly connected, at its lower portion, to an upper portion of oil phase-aqueous phase separator 9 so as for the liquid to be introduced from gas-liquid separator 8 into separator 9. In separator 9, the liquid is separated into the oil phase as an upper layer, which contains a produced cyclohexene, and the aqueous phase as a lower layer, which is comprised of the water and the hydrogenation catalyst suspended therein. The oil phase is withdrawn through oil phase outlet pipe 5. On the other hand, the aqueous phase is withdrawn through an aqueous phase outlet pipe provided at the lowermost portion of separator 9, and recycled through circulation pipe 10 to the inlet of reactor tube 4 by means of pump 11.

All the pipes have their respective flowmeters. Reactor tube 4 has a double-pipe structure comprised of an external pipe and an internal pipe. The temperature inside the internal pipe of reactor tube 4 is maintained at a constant temperature by passing steam for heating or water for cooling through the interstice between the internal pipe and the external pipe.

Hydrogenation reaction is carried out in substantially the same manner as in Example 1, except that a different reactor, i.e., reactor tube as described above is employed. Illustratively stated, first, the inside of the reactor tube is purged with nitrogen. After purging with nitrogen, an aqueous phase comprised of the same hydrogenation catalyst, water, $ZnSO_4 \cdot 7H_2O$ and powdery $ZrO_2$ in the same proportions as in Example 1 is charged in reactor tube 4, gas-liquid separator 8, oil phase-aqueous phase separator 9, pump 11 and circulation pipe 10. By means of pump 11, the aqueous phase is circulated at a flow rate of 50,000 liters/hr. Reactor tube 4 is heated by passing steam, and the inside temperature of reactor tube 4 is maintained at 140° C. Then, hydrogen gas is introduced under pressure into reactor tube 4 at a flow rate of 1,200 Nm$^3$/hr, while maintaining the internal total pressure of reactor tube 4 at 50 kg/cm$^2$ under steady operation conditions. A fresh benzene liquid is gradually fed at start-up and then at a flow rate of 2,000 kg/hr under steady operation conditions. The level of the oil phase-aqueous phase interface in separator 9 is maintained below the position of oil phase outlet pipe 5, and water is added through pipe 2 in an amount corresponding to the amount of water which is dissolved in the oil phase and withdrawn through oil phase outlet pipe 5. The level of the gas-liquid interface (free surface) in gas-liquid separator 8 is kept constant by controlling the amount of the withdrawn oil phase. After the entire reaction system has become steady, the composition of the oil phase withdrawn from oil phase outlet pipe 5 is analyzed. The analysis shows that the conversion of benzene is 55%, the selectivity for cyclohexene is 79% and the by-product is cyclohexane. These obtained values are the results of the reaction performed under the reaction rate-limiting conditions, and are found to be satisfactory. The maximum shear rate in reactor tube 4 is about 750/sec, and the oil globules therein have an average diameter of 0.5 mm. The separation of the oil phase from the aqueous phase is good, with no catalyst observed in the oil phase withdrawn from oil phase outlet pipe 5.

EXAMPLES 8 AND 9

Using the same apparatus as in Example 7, partial hydrogenation reactions are individually carried out under substantially the same reaction conditions as in Example 7, except that the aqueous phase is circulated at a flow rate of 80,000 liters/hr in Example 8 and at a flow rate of 30,000 liters/hr in Example 9. Results are good as shown in Table shown below.

COMPARATIVE EXAMPLE 3

Using the same apparatus as in Example 7, a partial hydrogenation reaction is carried out under substantially the same reaction conditions as in Example 7, except that the aqueous phase is circulated at a flow rate as low as 3,000 liters/hr, and that hydrogen gas is fed at a flow rate of 1,000 Nm$^3$/hr. A fresh benzene liquid is gradually fed at start-up and then at a flow rate of 2,000 kg/hr under steady operation conditions. The reaction system in reactor tube 4 is transported in the form of a flow of a double layer of a liquid phase layer (comprising an oil phase and an aqueous phase) and a separate gaseous phase layer, without the formation of fine gas bubbles and fine oil globules in the continuous aqueous phase. The volume of the gaseous phase is larger than that of the liquid phase. An analysis of the composition of an oil phase withdrawn from oil phase outlet pipe 5 shows that the conversion of benzene is 7%, the selectivity for cyclohexene is 60% and the by-product is cyclohexane. The maximum shear rate in reactor tube 4 is 38/sec.

EXAMPLE 10

Using the same hydrogenation catalyst as in Example 1, a partial hydrogenation reaction of benzene is carried out under the following conditions.

As a partial hydrogenation reactor, reactor 4 having a capacity of 8,000 liters as shown in FIG. 3 is used, which has an agitator with agitating turbine blades 7. Agitating turbine blades 7 include six blade sets arranged in tiers. Reactor 4 is partitioned by means of porous plate 14 as baffle means having a porosity of 5% into six chambers arranged in tiers so that each chamber contains one set of the blade sets. The porous plate 14 allows the reaction system to flow from a first chamber of every two mutually adjacent chambers partitioned by the porous plate 14 to a second chamber of the adjacent chambers in accordance with an upward flow direction of the reaction system, while the porous plate 14 prevents flow of the reaction system in a counter direction to that direction, so that the reaction system in the second chamber is prevented from being back-mixed with the reaction system in the first chamber. Reactor 4 has its inner surface coated with Teflon (trademark of polytetrafluoroethylene manufactured and sold by E.I. Du Pont De Nemours And Company, U.S.A.). Reactor 4 has, at its lower portion a thermometer protecting sheath (not shown). Reactor 4 is also provided with a common pipe for introducing benzene which is fed through pipe 1 and for introducing water which is fed through pipe 2, pipe 3 for feeding hydrogen gas, and a pressure gauge (not shown). Further, reactor 4 is provided, at an upper portion thereof, with a thermometer protecting sheath (not shown) and a pressure gauge (not shown). An upper portion of reactor 4 is fluidtightly connected to an upper portion of gas-liquid separator 8 so as for a reaction mixture produced in reactor 4 to be fed into gas-liquid separator 8. In gas-liquid separator 8, a gas comprised of hydrogen gas is separated from a liquid comprised of an oil phase and an aqueous phase. The gas is discharged through hydrogen gas discharge pipe 12. Gas-liquid separator 8 is fluidtightly connected, at its lower portion, to an upper portion of oil phase-aqueous phase separator 9 so as for the liquid to be introduced from separator 8 into separator 9. In separator 9, the liquid is separated into the oil phase as an upper layer, which contains a produced cyclohexene, and the aqueous phase as a lower layer, which is comprised of the water and the hydrogenation catalyst suspended therein. The oil phase is withdrawn through oil phase outlet pipe 5. On the other hand, the aqueous phase is withdrawn through an aqueous phase outlet pipe provided at the lowermost portion of separator 9, and recycled through circulation pipe 10 to a lower portion of reactor 4 by means of pump 11.

All the pipes have their respective flowmeters. Reactor 4 has an external jacket (not shown). The temperature inside reactor 4 is maintained at a constant temperature by passing steam for heating or water for cooling through the jacket.

Hydrogenation reaction is carried out in substantially the same manner as in Example 1, except that a different reactor as described above and shown in FIG. 3 is employed. Illustratively stated, first, the inside of the reactor is purged with nitrogen. After purging with nitrogen, an aqueous phase comprised of the same hydrogenation catalyst, water, $ZnSO_4 \cdot 7H_2O$ and powdery $ZrO_2$ in the same proportions as in Example 1 is charged in reactor 4, gas-liquid separator 8, oil phase-aqueous phase separator 9, pump 11 and circulation pipe 10. The agitator is operated at 90 rpm to agitate the charged aqueous phase. By means of pump 11, the aqueous phase is circulated at a flow rate of 25,000 liters/hr, and the temperature inside reactor 4 is elevated to 140° C. with steam. Then, hydrogen gas is introduced under pressure into reactor 4 to replace nitrogen gas for purging and to maintain the internal total pressure of reactor 4 at 50 $kg/cm^2$ under steady operation conditions. A fresh benzene liquid is gradually fed at start-up and then at a flow rate of 4,000 kg/hr under steady operation conditions. After the start of the reaction, water for cooling is introduced into the jacket so that the autoclave inner temperature is adjusted to 140° C. The level of the oil phase-aqueous phase interface in separator 9 is maintained below the position of oil phase outlet pipe 5, and water is added through pipe 2 in an amount corresponding to the amount of water which is dissolved in the oil phase and withdrawn through oil phase outlet pipe 5. The level of the gas-liquid interface (free surface) in gas-liquid separator 8 is kept constant by controlling the amount of the withdrawn oil phase. After the entire reaction system has become steady, the composition of the oil phase withdrawn from oil phase outlet pipe 5 is analyzed. The analysis shows that the conversion of benzene is 52%, the selectivity for cyclohexene is 81% and the by-product is cyclohexane. These obtained values are the results of the reaction performed under the reaction rate-limiting conditions, and are found to be satisfactory. The maximum shear rate in reactor 4 is about 600/sec, and the oil globules therein have an average diameter of 0.3 mm. The separation of the oil phase from the aqueous phase is good, with no catalyst observed in the oil phase withdrawn from oil phase outlet pipe 5.

TABLE

| Example and Comparative Example Nos. | Example 1 | Example 2 | Example 3 | Comparative Example 1 | Example 4-1 | Example 4-2 | Comparative Example 2-1 | Comparative Example 2-2 | Example 5 | Example 6-1 | Example 6-2 | Example 7 | Example 8 | Example 9 | Comparative Example 3 | Example 10 |
|---|---|---|---|---|---|---|---|---|---|---|---|---|---|---|---|---|
| Capacity of the reactor (liters) | 4 | 4 | 4 | 4 | 4000 | 4000 | 4000 | 4000 | 4000 | 4000 | 4000 | 4000 | 4000 | 4000 | 4000 | 8000 |
| Revolution rate of the agitation (rpm) | 600 | 490 | 800 | 60 | 108 | 108 | 200 | 200 | 45 | 175 | 175 | — | — | — | — | 90 |
| Flow rate of the continuous aqueous phase (liters/hr) | | | | | | | | | | | | 50000 | 80000 | 30000 | 3000 | — |
| Average diameter of oil globules (mm) | 0.1 | 0.15 | 0.05 | * | 0.2 | 0.2 | 0.015 | 0.015 | 24 | 0.04 | 0.04 | 0.5 | 0.3 | 1.2 | ** | 0.3 |
| Average diameter of gas bubbles (mm) | 1.5 | 1.8 | 1.0 | 10 | 2 | 2 | 0.3 | 0.3 | 13 | 0.6 | 0.6 | 3 | 2.4 | 4 | ** | 2.2 |
| Maximum shear rate (sec⁻¹) | 440 | 360 | 590 | 44 | 860 | 860 | 2200 | 2200 | 70 | 1800 | 1800 | 750 | 1200 | 440 | 38 | 600 |
| Conversion of benzene (%) | 38 | 38 | 37 | 4 | 39 | 38 | 38 | 24 | 37 | 32 | 30 | 55 | 53 | 56 | 7 | 52 |
| Selectivity for cyclohexene (%) | 80 | 79 | 81 | 45 | 80 | 81 | 81 | 79 | 78 | 82 | 82 | 79 | 80 | 78 | 60 | 81 |
| Volume ratio (oil phase/continuous aqueous phase) | 0.25 | 0.25 | 0.25 | 0.25 | 0.3 | 0.3 | 0.3 | 0.3 | 0.3 | 0.3 | 0.3 | 0.054 | 0.034 | 0.09 | 0.9 | 0.35 |

Note: * The oil phase is not dispersed and forms a continuous layer in the upper portion of the reaction system.
Note: ** In the reactor tube, the reaction system is transported in the form of a flow of a double layer of a liquid phase layer (comprising an oil phase and an aqueous phase) and a separate gaseous phase layer. The volume of the gaseous phase is larger than that of the liquid phase.

What is claimed is:

1. A method for continuously producing a cycloolefin by partially hydrogenating a monocyclic aromatic hydrocarbon, which comprises:

reacting a monocyclic aromatic hydrocarbon with hydrogen in the presence of a particulate hydrogenation catalyst comprised mainly of metallic ruthenium, in a reaction system comprising:

a continuous aqueous phase having the particulate hydrogenation catalyst suspended therein;

an oil phase containing the monocyclic aromatic hydrocarbon; and a gaseous phase comprising hydrogen gas, while applying a shearing force to the reaction system at a maximum shear rate of between about 50 and about 2000/sec, so that the oil phase and the gaseous phase are dispersed in the continuous aqueous phase as globules and as bubbles, respectively, thereby producing a reaction mixture comprising a liquid comprised of a product-containing oil phase and an aqueous phase;

separating said reaction mixture into said product-containing oil phase and said aqueous phase; and withdrawing said product-containing oil phase while recycling to said reaction system said aqueous phase containing the hydrogenation catalyst wherein the partial hydrogenation reaction is conducted with continued stable conversion of said aromatic hydrocarbon to said cycloolefin.

2. The method according to claim 1, wherein said metallic ruthenium has an average crystallite diameter of about 200 Å or less.

3. The method according to claim 1, wherein the volume ratio of said oil phase to said continuous aqueous phase is between about 0.01 and about 1.5.

4. The method according to claim 1, wherein the weight ratio of said hydrogenation catalyst to water present in said reaction system is between about 0.001 and about 0.2.

5. The method according to claim 1, wherein said reaction is performed at a temperature of between about 25° and about 250° C. under a hydrogen partial pressure of between about 5 and about 150 kg/cm$^2$.

6. The method according to claim 1, wherein the globules of said oil phase have an average diameter of between about 0.02 and about 30 mm.

7. The method according to claim 1, wherein the bubbles of said gaseous phase have an average diameter of between about 0.4 and about 20 mm.

8. The method according to claim 1, wherein said reaction is conducted in at least one reactor having an agitator with a plurality of agitating blades for producing said shearing force and wherein said agitator is operated so that the entire reaction system in said reactor is agitated to prevent the catalyst suspended in the continuous aqueous phase from settling and to divide aggregated gas bubbles and aggregated oil globules, formed in said reaction system at places distant from said agitating blades, into re-dispersed gas bubbles and re-dispersed oil globules, so that the dispersion of the gas phase as bubbles and the oil phase as globules in said continuous aqueous phase is maintained.

9. The method according to claim 8, wherein said reaction is conducted using a plurality of reactors connected in series and comprising a first reactor and at least one additional reactor, and wherein a reaction mixture, which is obtained in a reactor preceding said additional reactor and comprises a produced cycloolefin and an unreacted monocyclic aromatic hydrocarbon, is introduced to said additional reactor to thereby partially hydrogenate said unreacted monocyclic aromatic hydrocarbon.

10. The method according to claim 8 or 9, wherein said plurality of agitating blades include a plurality of blade sets arranged in tiers and wherein said blade sets comprise a first and a second blade set, said first blade set being disposed at the lowermost position for producing and dispersing the gas bubbles and the oil globules in said continuous aqueous phase and for mixing the gas bubbles and the oil globules in the entire reaction system, and said second blade set being disposed at a position such that when said agitator is operated, a gas present above a gas-liquid free surface in the reactor is caused to be engulfed into said reaction system below said free surface by the action of said second blade set.

11. The method according to claim 8 or 9, wherein said reactor has an outlet for a reaction product and has a weir around said outlet for providing a stationary zone for said reaction mixture to thereby facilitate separation of said reaction mixture into an upper oil layer comprising a produced cycloolefin and a lower aqueous layer having the catalyst suspended therein, followed by withdrawal of said upper oil layer while allowing said lower aqueous layer to flow down and bach into the reactor.

12. The method according to claim 1, wherein said reaction is performed while circulating said reaction system through a reactor tube at a flow rate sufficient to exert said shearing force.

13. The method according to claim 8 or 12, wherein said reaction mixture contains a gas comprised of hydrogen gas, and wherein said reaction mixture is introduced to a gas-liquid separator disposed outside said reactor to effect separation between the gas and the liquid, and said liquid is introduced to a product-containing oil phase-aqueous phase separator to thereby separate the product-containing oil phase as an upper layer containing a produced cycloolefin from the aqueous phase as a lower layer comprising the water and the catalyst suspended therein, followed by withdrawal of said product-containing oil phase while recycling said aqueous phase to said reactor.

14. The method according to any one of claims 1 to 7, wherein said reaction is conducted in a reactor having an agitator with a plurality of agitating blades for producing said shearing force, said plurality of agitating blades including a plurality of blade sets arranged in tiers, wherein said reactor is partitioned by means of baffle means into a plurality of chambers arranged in tiers so that each chamber contains at least one set of said blade sets, wherein said agitator is operated so that the entire reaction system in each chamber is agitated to prevent the catalyst suspended in the continuous aqueous phase from settling and to divide aggregated gas bubbles and aggregated oil globules, formed in said reaction system in each chamber at places distant from said agitating blades, into re-dispersed gas bubbles and re-dispersed oil globules, so that the dispersion of the gas phase as bubbles and the oil phase as globules in said continuous aqueous phase in each chamber is maintained, and wherein said baffle means allows the reaction system to flow from a first chamber of two mutually adjacent chambers partitioned by said baffle means to a second chamber of said adjacent chambers in accordance with a predetermined direction of flow of the reaction system, while said baffle means prevents flow of the reaction system in a counter direction to said predetermined direction, so that the reaction system in said second chamber is prevented from being back-mixed with the reaction system in said first chamber.

15. The method according to claim 14, wherein the uppermost chamber of said chambers has an outlet for a reaction product and has a weir around said outlet for providing a stationary zone for said reaction mixture to thereby facilitate separation of said reaction mixture into an upper oil layer comprising a produced cycloolefin and a lower aqueous layer having the catalyst suspended therein, followed by withdrawal of said upper oil layer to flow down and back into the reactor.

16. The method according to claim 14, wherein the uppermost chamber of said chambers contains an uppermost blade set of said blade sets which is disposed at a position such that when said agitator is operated, a gas present above a gas-liquid free surface in the reactor is caused to be engulfed into said reaction system below said free surface by the action of said uppermost blade set.

17. The method according to claim 14, wherein said reaction mixture contains a gas comprised of hydrogen gas, wherein said reaction mixture is introduced to a gas-liquid separator disposed outside of said reactor to effect separation between the gas and the liquid, and said liquid is introduced to a product-containing oil phase-aqueous phase separator to thereby separate the product-containing oil phase as an upper layer containing a produced cycloolefin from the aqueous phase as a lower layer comprising the water and the catalyst suspended therein, followed by withdrawal of said product-containing oil phase while recycling said aqueous phase to said reactor.

* * * * *

UNITED STATES PATENT AND TRADEMARK OFFICE
CERTIFICATE OF CORRECTION

PATENT NO(). : 5,457,251

DATED : October 10, 1995

INVENTOR(S) : Yamashita et al.

It is certified that error appears in the above-identified patent and that said Letters Patent is hereby corrected as shown below:

Column 31, the fourth line up from the bottom should end with a comma.

Column 32, in the last line, for "bach" read --- back ---.

Column 33, in the penultimate line, after "upper oil layer", insert --- while allowing said lower aqueous layer ---.

Signed and Sealed this

Eleventh Day of June, 1996

*Attest:*

BRUCE LEHMAN

*Attesting Officer*    *Commissioner of Patents and Trademarks*